United States Patent [19]
Kim et al.

[11] Patent Number: 6,030,979
[45] Date of Patent: Feb. 29, 2000

[54] PHARMACEUTICAL COMPOSITION COMPRISING 5,6-DIHYDRODIBENZO[A,G] QUINOLIZINIUM DERIVATIVES AND THE SALTS THEREOF

[75] Inventors: Jung Ho Kim, Daejeon; Tae Neung Jhong, Kyonggi-do; Young Ki Paik, Seoul; Joon Seo Park; Eui Deok Kim, both of Daejeon; You Suk Lee, Seoul; Seung Un Kim, Daejeon, all of Rep. of Korea

[73] Assignee: Hanwha Corporation, Seoul, China

[21] Appl. No.: 09/235,489

[22] Filed: Jan. 22, 1999

[30] Foreign Application Priority Data

Dec. 21, 1998 [KR] Rep. of Korea .................. 98-58722

[51] Int. Cl.[7] .................................................. A61K 31/44
[52] U.S. Cl. ........................ 514/280; 514/284; 514/824
[58] Field of Search ................................. 514/280, 284, 514/824

[56] References Cited

U.S. PATENT DOCUMENTS

| | | | |
|---|---|---|---|
| 3,835,140 | 9/1974 | Zee-Cheng et al. | 260/283 SY |
| 4,033,966 | 7/1977 | Sawa | 260/286 Q |
| 4,042,592 | 8/1977 | Sawa | 260/286 Q |
| 4,087,426 | 5/1978 | Shamma et al. | 260/286 R |
| 4,200,629 | 4/1980 | Nakamura | 424/195 |
| 4,761,417 | 8/1988 | Maroko | 514/284 |
| 4,761,477 | 8/1988 | Ikekawa et al. | 546/48 |
| 4,980,344 | 12/1990 | Maroko | 514/26 |

FOREIGN PATENT DOCUMENTS 2043218  9/1970  Germany .
64021530 of 1964  Japan .
1265627  8/1970  United Kingdom .

OTHER PUBLICATIONS

Fukuda et al., Chem. Pharm. Bull., vol. 18, No. 7, p. 1299–1304 (1970).

Naruto et al., Tetrahedron Lett., vol. 19, p. 1597–1600 (1976).

Karas–Gasparec et al., CA Accession No. 1968:46980 (1968).

Primary Examiner—Kimberly Jordan
Attorney, Agent, or Firm—Hunton & Williams

[57] ABSTRACT

The present invention provides a pharmaceutical composition comprising 5,6-dihydrodibenzo[a,g]quinolizinium derivative and the salts thereof of formula (I) which specifically inhibits the sterol 14-reductase which is involved in the distal pathway of cholesterol biosynthesis, and the use of the compound of formula (I) for treating hypercholesterolaemia or hyperlipidaemia.

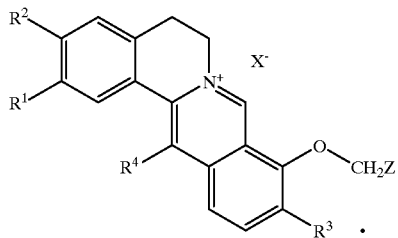

9 Claims, No Drawings

PHARMACEUTICAL COMPOSITION COMPRISING 5,6-DIHYDRODIBENZO[A,G] QUINOLIZINIUM DERIVATIVES AND THE SALTS THEREOF

TECHNICAL FIELD

The present invention relates to a pharmaceutical composition. More specifically, the present invention is directed to a pharmaceutical composition comprising 5,6-dihydrodibenzo[a,g]quinolizinium derivatives and the salts thereof which specifically inhibit sterol 14-reductase which is involved in the distal pathway of cholesterol biosynthesis, and thus exert cholesterol biosynthesis inhibiting effect. The present invention also relates to the use of 5,6-dihydrodibenzo[a,g]-quinolizinium derivatives and the salts thereof which are represented by formula (I) as set forth below for treating hypercholesterolemia or hyperlipidaemia.

BACKGROUND ART

Cholesterol is an important vital constituent of cell membrane in mammal and is involved in cell division, growth, development and control of differentiation, and also is a precursor of various essential metabolites (for example, steroid hormones, bile acids). However, it may cause hyperlipidaemia which leads to atherosclerosis if its intake or production within the body is excess. Hyperlipidaernia leads to cardiovascular disease which is a leading cause of death in humans. It is usually caused when cholesterol or triglyceride exceeds a proper level (i.e., total cholesterol level for adults at the age of between 30 and 40 is about 200 mg/dl), and then, is deposited to the inner wall of an artery to form atheroma plaques, thereby blood flow being inhibited which causes cardiac failure or cerebral stroke. Cholesterol is synthesized mainly in the liver in mammals and the synthetic pathway thereof is started from acetyl-CoA and is completed after at least 32 steps of enzymatic reactions.

Cholesterol biosynthesis which occurs in mammal can be summarized according to the enzyme reaction patterns in which each intermediate is formed as in the following reaction scheme 1.

Reaction Scheme 1

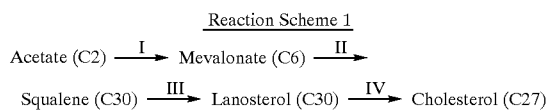

In the above reaction scheme, steps I and II undergo polymerization, and steps II and III undergo cyclization. In step IV, transformation, demethylation, isomerization or reduction of steroid ring is proceeded. Cholesterol biosynthesis is carefully controlled by the multi-step regulation, i.e., the so-called multivalent coordinate regulation. For example, 3-β-hydroxymethylglutaryl-CoA reductase (HMG-CoA reductase) is the main rate-limiting enzyme in the cholesterol biosynthesis. It reduces HMG-CoA synthesized from acetyl-CoA during the early stage of the biosynthetic pathway starting from acetate (C2) to mevalonate (C6) and is inhibited in vivo by the final product, cholesterol. More specifically, the activity of this enzyme is controlled by dietary cholesterol, oxysteroids and mevalonate derivatives in a feed-back inhibition manner. For the past decade, the lipid-lowering agents have been developed based on their inhibiting activities against this enzyme. Most of currently marketed therapeutic agents for hyperlipidaemia which have been developed based on such mechanism include, for example, statins such as lovastatin, pravastatin, simvastatin, atorvastatin, and cerivastatin. However, if cholesterol biosynthesis is suppressed by inhibiting the activity of HMG-CoA reductase which is the rate limiting enzyme at the early stage of cholesterol biosynthesis, there may be many side effects that the synthesis of many important biomolecules such as dolicol, isopentenyl pyrophosphate, haem A, and ubiquinone which are also derived from mevalonate are suppressed together.

Therefore, it may be advantageous to block cholesterol biosynthesis at a step distal to HMG-CoA reductase in order to prevent depletion of such essential intermediates.

Accordingly, recent researches have been focused on the development of new type of therapeutic agents for hyperlipidaemia which can effectively block only the post-squalene steps without interfering HMG-CoA reductase activity. For example, the activation mechanisms of the distal enzymes responsible for the post-squalene pathway in the cholesterol biosynthesis which comprises the sequence of 'squalene→lanosterol→zymosterol→desmosterol→ cholesterol' have been studied, and some attempts to screen and develop a drug which can specifically inhibit the activity of the target enzyme responsible for the distal pathway of cholesterol biosynthesis, have been made. Especially, based on the inhibitory activity of squalene epoxidase responsible for the pathway of 'squalene→lanosterol', a benzylamine series compound, NB598 has been developed by Banyu Pharmaceutical Co. of Japan; Squalenestatin I has been developed by the researchers of Glaxo Wellcome Limited, a British company on the basis of its inhibition of squalene synthase which is responsible for the synthesis of squalene from farnesyl pyrophosphate. RPR107393 has been developed as a potent squalene synthase inhibitor by researchers at Rhone-Poulenc, France. Further, Taton et al. have reported MDL 28,815 having 8-azadecaline ring based on the inhibition of 2,3-oxidosqualene cyclase responsible for the cyclization reaction in which squalene epoxide is converted into methylsterol (See, Biochem. Biophys. Res. Commun. 1986, 138, 764–70). These NB598, Squalenestatin I, RPR107393 and MDL 28,815 which inhibit the activities of enzymes responsible for the post-mevalonate pathway in the cholesterol biosynthetic pathway have a merit that they can selectively inhibit the cholesterol biosynthesis without effecting on the production of other important intermediates which are derived from mevalonate, differently from the drugs that target HMG-CoA reductase responsible for the early stage of cholesterol biosynthesis.

However, these agents have not yet been commercialized as therapeutic gents for hyperlipidaemia.

DISCLOSURE OF THE INVENTION

The present inventors have conducted an extensive research for many years in order to develop a novel class of cholesterol biosynthetic inhibitor which specifically inhibits the enzyme involved in the step of 'lanosterol→cholesterol'. As a result, the inventors have surprisingly discovered that 5,6-dihydrodibenzo-[a,g]quinolizinium derivatives and the salts thereof which are represented by formula (I) as set forth hereinafter strongly inhibit the activity of sterol 14-reductase which catalyzes the reduction of 4,4-dimethyl-8,14-dien-3β-ol and thus have completed the present invention.

Based on this findings, it was possible to provide a cholesterol biosynthesis inhibitor which comprises 5,6-dihydrodibenzo[a,g]quinolizinium derivatives and the salts thereof which are represented by formula (I) as the main component which specifically inhibits the sterol 14-reductase in the distal pathway of the cholesterol biosynthesis.

It is therefore an object of the present invention to provide 5,6-dihydrodibenzo[a,g]quinolizinium derivatives or the salts thereof which are represented by formula (I) as set forth below.

Another object of the present invention is to provide a cholesterol biosynthesis inhibitor which comprises 5,6-dihydrodibenzo[a,g]quinolizinium derivatives and the salts thereof which are represented by formula (I).

Further object of the present invention is to provide a pharmaceutical composition for treating hyperlipidaemia which comprises 5,6-dihydro-dibenzo[a,g]quinolizinium derivatives and the salts thereof which are represented by formula (I) and a pharmaceutically acceptable excipient.

Still another object of the present invention is to provide a method for treating hyperlipidaemia by inhibiting cholesterol biosynthesis, especially inhibiting sterol 14-reductase with the above pharmaceutical composition.

Further objects and advantages of the invention will become apparent through reading the remainder of the specification.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the detailed description of the preferred embodiment in addition to the scope of the invention defined by the Claims.

Hereinbelow, the application will be illustrated in more detail.

5,6-Dihydrodibenzo[a,g]quinolizinium derivatives and the salts thereof according to the present invention have the similar chemical structure to the coridaline-series alkaloids in the form of quaternary ammonium salt which are major active components of *Corydalis Turtschaninowii Besser*. *Corydalis Turtschaninowii Besser* is an annual plant widely distributed in the mountains and fields of Korea and has been used in the prescription of sedative agent or hemostatic agent in herbal medicine. This coridaline in the form of a quaternary ammonium salt has been known to have a week sedative action and a strong gastric juice secretion action, and UK Patent No. 1,265,627 and German Patent No. 2,043,218 disclose its use as an anti-ulcer agent.

The inventors of the present invention have discovered the novel compound of the present invention in the course of screening new cholesterol biosynthesis inhibitor.

This discovery was fully supported by a screening method for the activity of sterol 14-reductase that was established by the inventors since the inventors have started the research for a new drug.

The detailed screening method will be explained in detail in the working examples. Thus, the principle thereof will be briefly explained below.

That is, sterol 14-reductase is one of the main regulatory enzymes for lanosterol→cholesterol pathway and is responsible for reduction of the double bond formed when a methyl group attached to the carbon at 14-position of lanosterol is demethylated. First, a screening system for sterol 14-reductase was constructed in which 4,4-dimethyl-5α-cholesta-7,14-dien-3β-ol is used as a substrate and then, the effect on the activity of sterol 14-reductase was investigated in the screening system. It is possible to obtain the correlation that a substance inhibiting the activity of sterol 14-reductase inhibits cholesterol biosynthesis by comparing the results obtained from the screening tests with those of the actual animal experiments.

Dibenzo[a,g]quinolizinium derivative for the purpose of the present invention can be represented by the formula (I) below.

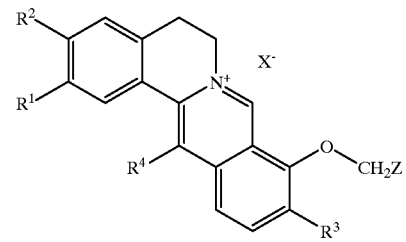

wherein, $R^1$ and $R^2$ which may be the same or different from each other, represent hydroxy group or an alkoxy group having 1 to 4 carbons or $R^1$ and $R^2$ together represent a methylenedioxy group;

$R^3$ represents a hydroxy group or an alkoxy group having 1 to 4 carbons;

$R^4$ represents a hydrogen atom, an alkyl group having 1 to 8 carbons, or an alkenyl group having 3 to 8 carbons;

X represents inorganic acid ion, organic acid ion or halide, more particularly, nitrate, sulfate, acetate, tartrate, maleate, succinate, citrate, furmarate, aspartate, salicylate, glycerate, ascorbate, fluoride, chloride, iodide or bromide, Z represents an alkyl group having 5 to 12 carbon, or an alkenyl group having 4 to 6 carbon, a N-benzotriazolyl group, a quinolinyl group, a furyl group, a substituted furyl group, or a group represented by the formula

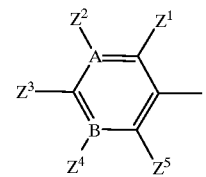

wherein $Z^1$, $Z^2$, $Z^3$, $Z^4$ and $Z^5$ which may be the same or different from each other, represent a hydrogen atom, halogen, an alkyl group having 1 to 5 carbons, a trifluoromethyl group, a phenyl group, a substituted phenyl group, a nitro group, an alkoxy group having 1 to 4 carbons, a methylenedioxy group, a trifluoro-methoxy group, a hydroxy group, a benzyloxy group, a phenoxy group, a vinyl group, a benzenesulfonylmethyl group or a methoxycarbonyl group; and A and B which may be the same or different from each other, represent carbon or nitrogen.

The cholesterol biosynthesis inhibitor according to the present invention, especially 5,6-dihydrodibenzo[a,g] quinolizinium derivatives or the salts thereof as the inhibitor of sterol 14-reductase can preferably be represented by Table 1 below:

TABLE 1
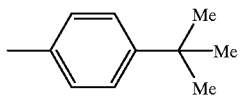
Formula Ia
| Comp. no. | R¹ | R² | R³ | R⁴ | Z | X | m.p. (° C.) |
|---|---|---|---|---|---|---|---|
| 1 | OMe | OMe | OMe | Et | —CH$_2$(CH$_2$)$_{10}$CH$_3$ | Cl | 150 |
| 2 | OMe | OMe | OMe | Et | 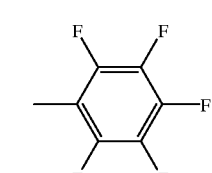 | Cl | 102 |
| 3 | OMe | OMe | OMe | Et | 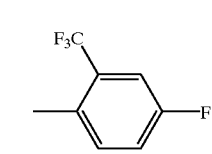 | Cl | 72 |
| 4 | OMe | OMe | OMe | Et | 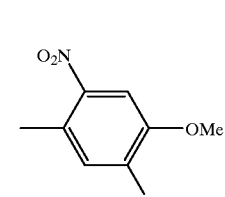 | Cl | 210 |
| 5 | OMe | OMe | OMe | Et | 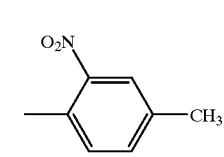 | Cl | 100 |
| 6 | OMe | OMe | OMe | Et | 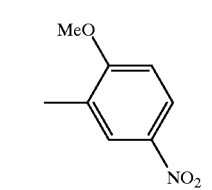 | Cl | 85 |
| 7 | OMe | OMe | OMe | Et | 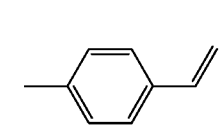 | Cl | 175 |
| 8 | OMe | OMe | OMe | Et | 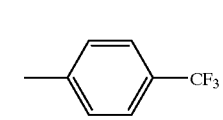 | Cl | 82 |
| 9 | OMe | OMe | OMe | Et |  | Cl | 115 |

TABLE 1-continued

Formula Ia

| Comp. no. | R¹ | R² | R³ | R⁴ | Z | X | m.p. (° C.) |
|---|---|---|---|---|---|---|---|
| 10 | OMe | OMe | OMe | Et | 2-Cl-4-F-phenyl | Cl | 76 |
| 11 | OMe | OMe | OMe | Et | 3-CF₃-phenyl | Cl | 117 |
| 12 | OMe | OMe | OMe | Et | 3-OMe-phenyl | Cl | 70 |
| 13 | OMe | OMe | OMe | Et | 2,3,5,6-tetrafluoro-4-CF₃-phenyl | Cl | 85 |
| 14 | OMe | OMe | OMe | Et | 4-OBn-phenyl | Cl | 71 |
| 15 | OMe | OMe | OMe | Et | 2,4-diMe-phenyl | Cl | 72 |
| 16 | OMe | OMe | OMe | Et | 4-Ph-phenyl | Cl | 83 |
| 17 | OMe | OMe | OMe | Et | 6-Cl-pyridin-3-yl | Cl | 114 |

TABLE 1-continued
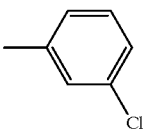
Formula Ia
| Comp. no. | R¹ | R² | R³ | R⁴ | Z | X | m.p. (° C.) |
|---|---|---|---|---|---|---|---|
| 18 | OMe | OMe | OMe | Et | 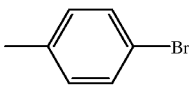 | Cl | 165 |
| 19 | OMe | OMe | OMe | Et | 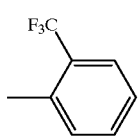 | Cl | 186 |
| 20 | OMe | OMe | OMe | Et | 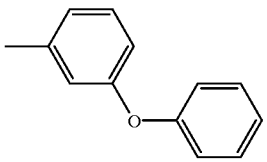 | Cl | 72 |
| 21 | OMe | OMe | OMe | Et | 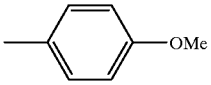 | Cl | 76 |
| 22 | OMe | OMe | OMe | Et | 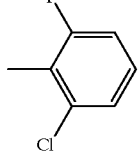 | Cl | 75 |
| 23 | OMe | OMe | OMe | Et | 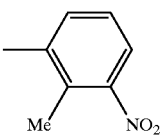 | Cl | 92 |
| 24 | OMe | OMe | OMe | Et | 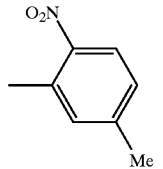 | Cl | 131 |
| 25 | OMe | OMe | OMe | Et |  | Cl | 98 |
| 26 | OMe | OMe | OMe | Et | —CH=CH₂ | Cl | 91 |

TABLE 1-continued

Formula Ia

| Comp. no. | R¹ | R² | R³ | R⁴ | Z | X | m.p. (° C.) |
|---|---|---|---|---|---|---|---|
| 27 | OMe | OMe | OMe | Et | 2,4-dimethylphenyl | Cl | 167 |
| 28 | OMe | OMe | OMe | Et | 2,5-dimethylphenyl | Cl | 87 |
| 29 | OMe | OMe | OMe | Et | 1H-benzotriazol-1-yl | Cl | 89 |
| 30 | OMe | OMe | OMe | Et | 4-isopropylphenyl | Cl | 85 |
| 31 | OMe | OMe | OMe | Et | 4-methylphenyl | Cl | 87 |
| 32 | OMe | OMe | OMe | Et | 3-methylphenyl | Cl | 76 |
| 33 | OMe | OMe | OMe | Et | 2-(trifluoromethyl)phenyl | Cl | 85 |
| 34 | OMe | OMe | OMe | Et | 3-bromophenyl | Cl | 95 |

TABLE 1-continued

Formula Ia

| Comp. no. | R¹ | R² | R³ | R⁴ | Z | X | m.p. (° C.) |
|---|---|---|---|---|---|---|---|
| 35 | OMe | OMe | OMe | Et | 2,5-dimethoxyphenyl | Cl | 135 |
| 36 | OMe | OMe | OMe | Et | quinolin-2-yl | Cl | 104 |
| 37 | OMe | OMe | OMe | Et | 3,4,5-trimethoxyphenyl | Cl | 110 |
| 38 | OMe | OMe | OMe | Et | 5-nitrofuran-2-yl | Cl | 100 |
| 39 | OMe | OMe | OMe | Et | 5-nitrofuran-2-yl | Cl | 85 |
| 40 | OMe | OMe | OMe | Et | 6-chloro-benzo[1,3]dioxol-5-yl | Cl | 105 |
| 41 | OMe | OMe | OMe | Et | 2-methylprop-1-enyl (Me, =CH₂) | Cl | 195 |
| 42 | OMe | OMe | OMe | Et | 4-(trifluoromethoxy)phenyl | Cl | 103 |
| 43 | OMe | OMe | OMe | Et | 2-iodophenyl | Cl | 110 |

TABLE 1-continued
Formula Ia
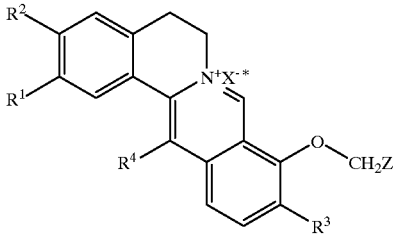
| Comp. no. | R¹ | R² | R³ | R⁴ | Z | X | m.p. (° C.) |
|---|---|---|---|---|---|---|---|
| 44 | OMe | OMe | OMe | Et | 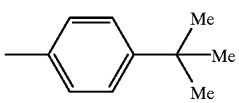 | Cl | 195 |
| 45 | —O—CH₂—O— | | OMe | Et | —CH₂(CH₂)₁₀CH₃ | I | 175 |
| 46 | —O—CH₂—O— | | OMe | Et | 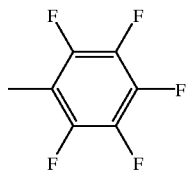 | I | 155 |
| 47 | —O—CH₂—O— | | OMe | Et | 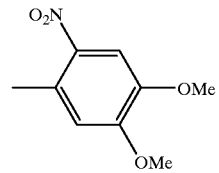 | I | 112 |
| 48 | —O—CH₂—O— | | OMe | Et | 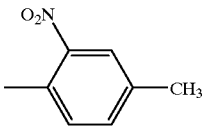 | I | 132 |
| 49 | —O—CH₂—O— | | OMe | Et | 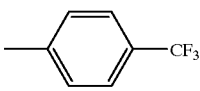 | I | 115 |
| 50 | —O—CH₂—O— | | OMe | Et | 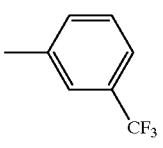 | I | 142 |
| 51 | —O—CH₂—O— | | OMe | Et | 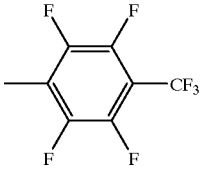 | I | 134 |
| 52 | —O—CH₂—O— | | OMe | Et | | I | 136 |

TABLE 1-continued
Formula Ia
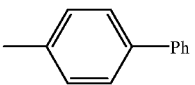
| Comp. no. | R¹ | R² | R³ | R⁴ | Z | X | m.p. (° C.) |
|---|---|---|---|---|---|---|---|
| 53 | —O—CH₂—O— | | OMe | Et | 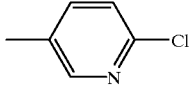 | I | 115 |
| 54 | —O—CH₂—O— | | OMe | Et | 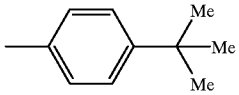 | I | 139 |
| 55 | OEt | OEt | OMe | Et | 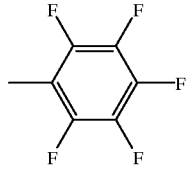 | Cl | 132 |
| 56 | OEt | OEt | OMe | Et | 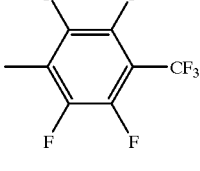 | Cl | 100 |
| 57 | OEt | OEt | OMe | Et | 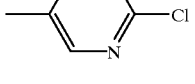 | Cl | 113 |
| 58 | OEt | OEt | OMe | Et | 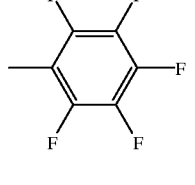 | Cl | 126 |
| 59 | OH | OH | OMe | Et | 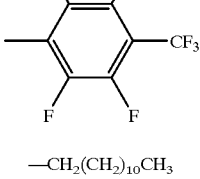 | Cl | 82 |
| 60 | OH | OH | OMe | Et | | Cl | 88 |
| 61 | OEt | OEt | OEt | Et | —CH₂(CH₂)₁₀CH₃ | Cl | 174 |

TABLE 1-continued

Formula Ia

| Comp. no. | R¹ | R² | R³ | R⁴ | Z | X | m.p. (° C.) |
|---|---|---|---|---|---|---|---|
| 62 | OEt | OEt | OEt | Et | —C₆H₄-4-CF₃ | Cl | 142 |
| 63 | OEt | OEt | OEt | Et | —C₆H₄-3-CF₃ | Cl | 127 |
| 64 | OEt | OEt | OEt | Et | —C₆F₄-CF₃ | Cl | 110 |
| 65 | OEt | OEt | OEt | Et | 5-methyl-2-chloropyridinyl | Cl | 136 |
| 66 | OPr | OPr | OPr | Et | —C₆H₄-4-C(Me)₃ | Cl | 133 |
| 67 | OPr | OPr | OPr | Et | —C₆F₅ | Cl | 122 |
| 68 | OPr | OPr | OPr | Et | —C₆H₄-4-CF₃ | Cl | 151 |
| 69 | OMe | OMe | OMe | Et | —C₆H₄-4-C(Me)₃ | HSO₄⁻ | 123 |
| 70 | OMe | OMe | OMe | Et | —C₆F₅ | CH₃CO₂⁻ | 108 |

TABLE 1-continued

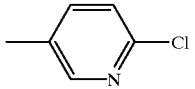

Formula Ia

| Comp. no. | R¹ | R² | R³ | R⁴ | Z | X | m.p. (° C.) |
|---|---|---|---|---|---|---|---|
| 71 | OMe | OMe | OMe | Et | (5-methyl-2-chloropyridinyl) | $NO_3^-$ | 127 |

The compounds represented by the formula (I) according to the present invention can be synthesized starting from the compound of formula (II) below according to the reaction scheme 2 described below.

Reaction Scheme 2

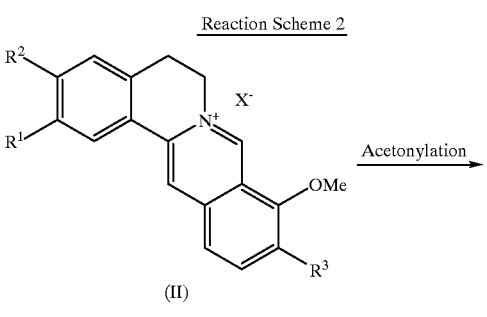

(II)

↓ Acetonylation

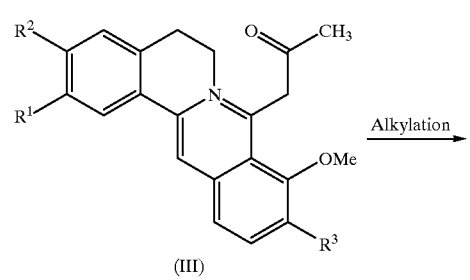

(III)

↓ Alkylation

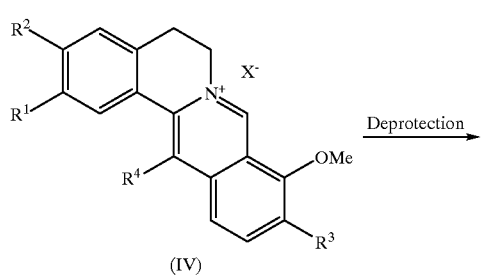

(IV)

↓ Deprotection

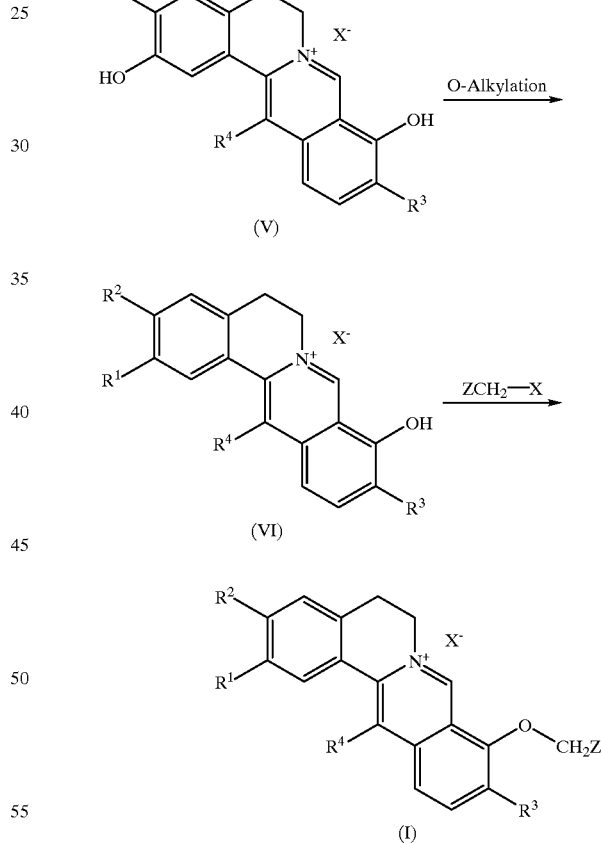

wherein, $R^1$, $R^2$, $R^3$, $R^4$, X and Z are the same as defined in the compound of formula (I) above.

In the first step of the reaction scheme, 5,6-dihydrodibenzo[a,g]quinolizinium salt of formula (II) is reacted with acetone in the presence of a base such as sodium hydroxide to give 8-acetonyl-5,6-dihydrodibenzo[a,g]quinolizine compound of the formula (III).

In the second step, 8-acetonyl-5,6-dihydrodibenzo[a,g] quinolizine compound and alkyl halide ($R^4$-X) are reacted at 50–100 °C. in a polar solvent such as acetonitrile or a non-polar solvent such as toluene to give 13-alkyl-5,6-dihydrodibenzo[a,g]quinolizinium salt of formula (IV).

The third step of the above reaction scheme involves the cleavage reaction of 2,3-methylenedioxy ring or deprotection reaction of 2,3-dimethoxy group in which the compound of formula (IV) is reacted with Lewis acid such as anhydrous aluminum chloride at 80–160 °C. and then subjected to hydrolysis reaction with a dilute acid. According to the reaction conditions, 13-alkyl-2,3-dihydroxy compound may be produced as a major product along with 2,3,9-trihydroxy-, or 2,3,9,10-tetrahydroxy compound and these compounds can be separated by recrystallization or column chromatography. However, it may be possible to use the compound in the fourth step reaction without further separation process.

The fourth step involves a reaction in which the compound of formula (V) obtained from the previous step is selectively allylated at 2,3-positions with an alkylating reagent such as dimethyl sulfate or iodomethane or reacted with dibromomethane to give 13-alkyl-9-hydroxy-5,6-dihydrodibenzo[a,g]quinolizinium salt of formula (VI) wherein a methylenedioxy ring is introduced.

In the fifth reaction step, the compound of formula (VI) thus obtained is reacted with electrophiles ($ZCH_2$-X) to give 9-substituted 5,6-dihydrodibenzo[a,g]-quinolizinium salt.

The compound of formula (IV) used in preparing the compound of formula (I) may also be synthesized under the different reaction condition according to the reaction scheme 3 below.

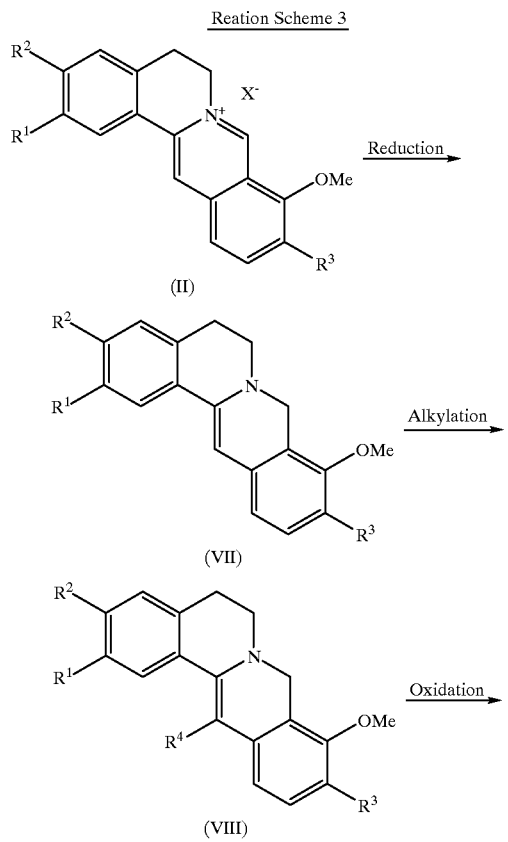

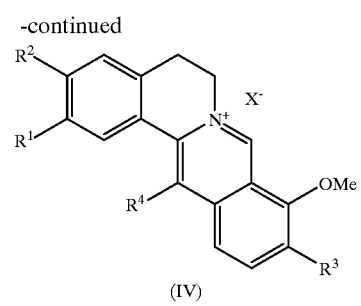

wherein, $R^1$, $R^2$, $R^3$, $R^4$ and X are the same as defined in the compound of formula (I) above.

According to the reaction scheme 3, 1.0 mol of 5,6-dihydrodibenzo[a,g]-quinolizinium salt of the formula (II) is reacted with 1.0 to 3.0 mol of $NaBH_4$ and 2.0 to 4.0 mol of potassium carbonate in an alcoholic solvent to give a compound of the formula (VII) and the compound thus obtained is then reacted with 1.0 to 3.0 mol of electrophiles ($R^4$-X) in an organic solvent to give 13-alkyl-dibenzo-[a,g] quinolizinium salt of the formula (VIII). Compound (VIII) is then oxidized with N-chlorosuccin imide (NCS) or N-bromosuccin imide to give 13-substituted 5,6-dihydrodibenzo[a,g]quinolizinium salt of the formula (IV).

In addition, the compound of formula (I) may also be synthesized under the different reaction condition according to the reaction scheme 4 below.

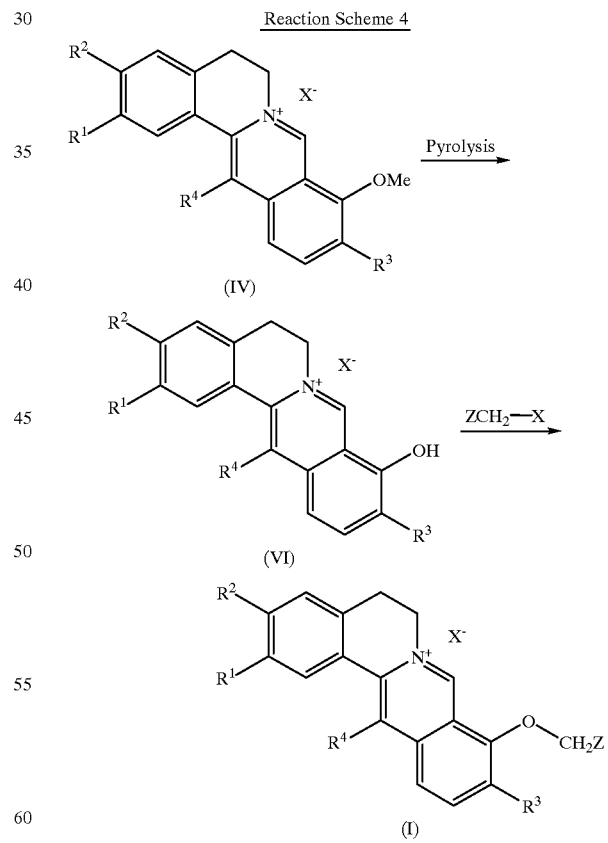

wherein, $R^1$, $R^2$, $R^3$, $R^4$, X and Z are the same as defined in the compound of formula (I) above.

According to the reaction scheme 4, 1.0 mol of the compound of the formula (IV) is subjected to pyrolysis in the presence of a non-polar solvent such as decaline or in the absence of a solvent at a high temperature of 100 to 300° C. to give a compound of the formula (VI) and the compound thus obtained is then reacted with 1.0 to 2.0 mol of electrophiles ($ZCH_2$-X) to give 9-substituted 5,6-dihydrodibenzo [a,g]quinolizinium salt of the formula (I).

9-Substituted 5,6-dihydrodibenzo[a,g]quinolizinium salt of the formula (I) may be transformed into various salts such as halide, sulfate, nitrate, acetate, cinnamate, tinate, tannate, maleate, succinate, citrate, fulmarate or fatty acid salt, etc. on the basis of the salts used in the purification process of the reaction scheme 5 described below.

Reaction Scheme 5

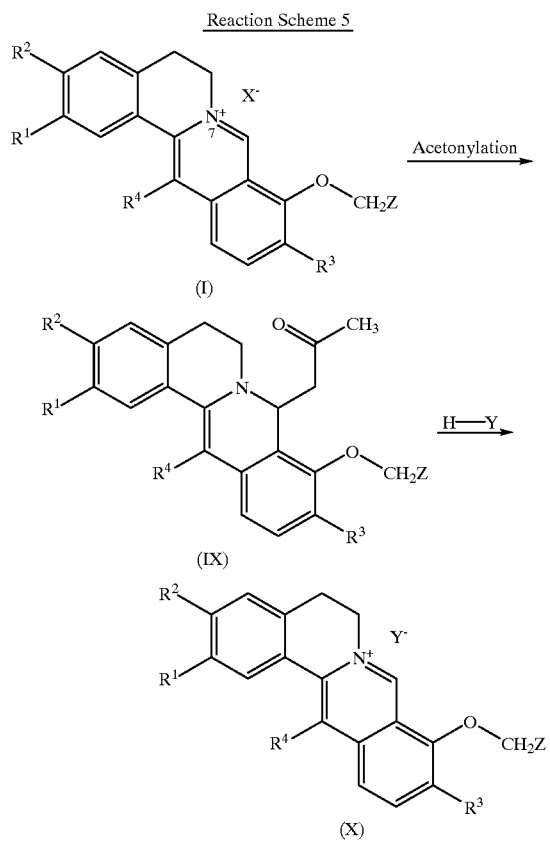

wherein, $R^1$, $R^2$, $R^3$, $R^4$, X and Z are the same as defined in the compound of formula (I) above, and Y represent halide, sulfate, nitrate, cinnamate, tinate, tannate, maleate, succinate, citrate, fumarate, or fatty acid salt ion.

In the above reaction scheme, substituted 5,6-dihydrodibenzo[a,g]quinolizinium salt of the formula (I) is reacted with acetone in the presence of a base such as sodium hydroxide to give 8-acetonyl-5,6-dihydrodibenzo[a, g]quinolizine compound of the formula (IX) and the compound thus obtained is reacted with a suitable inorganic acid, organic acid or fatty acid to give various 5,6-dihydrodibenzo [a,g]-quinolizinium compounds of formula (X).

Among 5,6-dihydrodibenzo[a,g]-quinolizinium salts of formula (I), the compound wherein $R^1$, $R^2$, $R^3$, $R^4$ and X each represents a methoxy group, a methoxy group, a methoxy group, an ethyl group and chloride, and Z represents 4-(tert-butyl)phenyl; the compound wherein $R^1$, $R^2$, $R^3$, $R^4$ and X each represents a methoxy group, a methoxy group, a methoxy group, an ethyl group and chloride, and Z represents 4-pentafluorophenyl; the compound wherein $R^1$, $R^2$, $R^3$, $R^4$ and X each represents a methoxy group, a methoxy group, a methoxy group, an ethyl group and chloride, and Z represents 4-trifluoromethylphenyl; and the compound wherein $R^1$–$R^2$, $R^3$, $R^4$ and X each represents a methylenedioxy group, a methoxy group, an ethyl group and iodide, and Z represents 4-trifluoromethylphenyl are preferred in an aspect of the pharmaceutical efficacy.

The compound of formula (I) markedly inhibits the cholesterol biosynthesis in the cultured human liver cell culture (HepG2 cell line). In order to investigate the effect of the compound of formula (I) of the invention, the compound was orally administered into male Syrian Golden Hamsters having weights of 90–110 g for two weeks and blood was then taken from each animal. Plasma lipids, i.e., total cholesterol, LDL-cholesterol, HDL-cholesterol and triglycerides were analyzed using an automatic analyzer (Automatic analyzer model Hitachi 7150). As the results, total cholesterol, LDL-cholesterol, and triglyceride levels were significantly decreased while HDL-cholesterol value was not significantly changed. In addition, the compound resulted in decrease in a certain degree in the glucose value within the serum.

The compound of formula (I) may be formulated into a pharmaceutical composition with pharmaceutically acceptable excipients or carriers. Especially, the composition can desirably be used as the therapeutic agents for treating hypercholesterolemia and hyperlipidaemia by inhibiting sterol 14-reductase. The composition may be formulated into a tablet, a syrup or an injection formulation, and thus, can be administered orally or parenterally. An effective dose will vary depending upon the kind of the excipients or carriers within the range for treating hypercholesterolemia and hyperlipidaemia with a dose of 0.1–50 mg/kg/day of active ingredient being preferable in case of oral administration.

BEST MODE FOR CARRYING OUT THE INVENTION

The present invention will be described in greater detail by way of the following examples and synthetic examples. The examples are provided for the purpose of illustration only and should not be construed as limiting the invention which is properly delineated in the Claims.

SYNTHETIC EXAMPLES

Hereinbelow, synthetic examples for the derivative of the compounds represented by the above formula (I) will be described.

Example 1

Preparation of 5,6-dihydro-2,3-dimethoxybenzo[a]-9-dodecoxy-13-ethyl-10-methoxybenzo[g] quinolizinium chloride (Compound No. 1)

10 G of 5,6-dihydro-2,3-methylenedioxybenzo[a]-9,10-dimethoxy-13-ethyl-benzo[g]quinolizinium chloride and 10 g of aluminum chloride were suspended in 70 ml of dichloromethane and the mixture was stirred for 1 hour. The reaction mixture was concentrated under reduced pressure to remove the solvent. A 15% hydrochloric acid solution was added to the mixture and the precipitate produced was filtered, washed and dried to give 9 g of 5,6-dihydro-2,3-dihydroxybenzo[a]-13-ethyl-9-hydroxy-10-methoxybenzo [g]quinolizinium chloride as a light orange crystal.

10 G of 5,6-dihydro-2,3-dihydroxybenzo[a]-1 3-ethyl-9-hydroxy-10-methoxybenzo[g]quinolizinium chloride were suspended in 150 ml of water and 20 g of a 50% sodium hydroxide solution and 20 ml of dimethylsulfate were added thereto. After the mixture was stirred for 5 hours, a 15% hydrochloric acid solution was added to adjust pH to neutral. The precipitate thus produced was filtered to give 8 g of 5,6-dihydro-2,3-dimethoxybenzo[a]-13-ethyl-9-hydroxy-10-methoxybenzo-[g]quinolizinium chloride as a light brown crystal. 1 G of 5,6-dihydro-2,3-dimethoxybenzo[a]-13-ethyl-9-hydroxy-10-methoxybenzo[g]quinolizinium chloride, 0.45 g of sodium iodide, and 0.41 g of potassium carbonate were dissolved in 10 ml of acetonitrile. After 0.7 g of dodecyl bromide was then added thereto, the mixture was refluxed for 8 hours. Undissolved by-products were filtered off and the filtrate was concentrated under reduced pressure to remove the solvent. The residue was then dissolved in chloroform and washed with 10 ml of water. The solution was dried over magnesium sulfate to remove water and the residue was then purified by silica gel column chromatography eluting with a mixed solvent of chloroform/methanol (15:1) to give 0.24 g of the titled compound as a brown crystal (m.p.: 150° C.).

$^1$H-NMR (300 MHz, CDCl$_3$) δ: 0.87(t, J=6.9 Hz, 3H), 1.26(m, 12H), 1.50(m, 4H), 1.68(t, J=7.2 Hz, 3H), 1.98(m, 4H), 3.35(m, 2H), 3.41(m, 2H), 3.96(s, 3H), 4.00(s, 3H), 4.01(s, 3H), 4.50(t, J=6.9Hz, 2H), 5.10(m, 2H), 6.91(s, 1H), 7.29(s, 1H), 8.01(d, J=9.3 Hz, 1H), 8.13(d, J=9.3 Hz, 2H), 10.00(s, 1H)

Example 2

Preparation of 5,6-dihydro-2,3-dimethoxybenzo[a]-9-[4-(tert-butyl)benzyloxy]-13-ethyl-10-methoxybenzo[g]quinolizinium chloride (Compound No. 2)

The process of Example 1 was repeated except that 0.6 g of 4-(tert-butyl)benzyl bromide was employed in place of dodecyl bromide to give 0.47 g of the titled compound as a brown crystal (m.p.: 102° C.).

$^1$H-NMR (300 MHz, CDCl$_3$) δ: 1.29(s, 9H), 1.69(t, J=7.2 Hz, 3H), 3.20(m, 2H), 3.39(m, 2H), 3.94(s, 3H), 3.99(s, 3H), 4.11(s, 3H), 4.98(m, 2H), 5.53(s, 2H), 6.95(s, 1H), 7.23(s, 1H), 7.42(d, J=8.1Hz, 2H), 7.64(d, J=8.1 Hz, 2H), 8.04(d, J=9.3 Hz, 1H), 8.87(d, J=9.3 Hz, 1H), 10.00(s, 1H)

Example 3

Preparation of 5,6-dihydro-2,3-dimethoxybenzo[a]-13-ethyl-10-methoxy-9-(2,3,4,5,6-pentafluoro)benzyloxybenzo[g]quinolizmiurn chloride (Compound No. 3)

The process of Example 1 was repeated except that 0.7 g of 2,3,4,5,6-pentafluorobenzyl bromide was employed in place of dodecyl bromide to give 0.80 g of the titled compound as a brown crystal (m.p.: 72° C.).

$^1$H-NMR (300 MHz, CDCl$_3$) δ: 1.67(t, J=7.8Hz, 3H), 3.37(m, 2H), 3.42(m, 2H), 3.96(s, 1H), 4.01(s, 3H4), 4.08(s, 3H), 5.06(m, 2H), 5.86(s, 2H), 6.93(s, 1H), 7.28(s, 1H), 7.92(d, J=9.3 Hz, 1H), 8.04(d, J=9.3 Hz, 1H), 10.12(s, 1H).

Example 4

Preparation of 5,6-dihydro-2,3-dimethoxybenzo[a]-13-ethyl-9-[4-fluoro-2-(trifluoromethyl)benzyloxy]-10-methoxybenzo[g]-quinolizinium chloride (Compound No. 4)

The process of Example 1 was repeated except that 0.68 g of 4-fluoro-2-(trifluoromethyl)benzyl bromide was employed in place of dodecyl bromide to give 0.76 g of the titled compound as a brown crystal (m.p.: 210° C.).

$^1$H-NMR (300 MHz, CDCl$_3$) δ: 1.68(t, J=6.6 Hz, 3H), 3.28(m, 2H), 3.41(m, 2H), 3.96(s, 3H), 4.00(s, 3H), 4.05(s, 3H), 5.05(m, 2H), 5.77(s, 2H), 6.94(s, 1H), 7.26(s, 1H), 7.40(m, 1H), 7.46(m, 1H), 7.97(d, 1H, J=9.3 Hz), 8.04(d, J=9.3 Hz, 1H), 8.50(m, 1H), 10.06(s, 1H).

Example 5

Preparation of 5,6-dihydro-2,3-dimethoxybenzo[a]-9-(4,5-dimethoxy-2-nitro)benzyloxy-13-ethyl-10-methoxybenzo[g]-quinolizinium chloride (Compound No. 5)

The process of Example 1 was repeated except that 0.75 g of 4,5-dimethoxy-2-nitrobenzyl bromide was employed in place of dodecyl bromide to give 0.36 g of the titled compound as a brown crystal (m.p.: 100° C.).

$^1$H-NMR (300 MHz, CDCl$_3$) δ: 1.60(t, J=7.2 Hz, 3H), 3.21(m, 2H), 3.39(m, 2H), 3.96(s, 3H), 3.98(s, 3H), 4.00(s, 3H), 4.13(s, 3H), 4.22(s, 3H), 5.18(m, 2H), 5.79(s, 2H), 6.91(s, 1H), 7.22(s, 1H), 7.43(s, 1H), 7.69(s, 1H), 7.91(d, J=9.0 Hz, 1H), 8.00(d, J=9.0 Hz, 1H), 10.36(s, 1H).

Example 6

Preparation of 5,6-dihydro-2,3-dimethoxybenzo[a]-13-ethyl-10-methoxy-9-(4-methyl-3-nitro)benzyloxybenzo[g]quinolizinium chloride (Compound No. 6)

The process of Example 1 was repeated except that 0.51 g of 4-methyl-3-nitrobenzyl chloride was employed in place of dodecyl bromide to give 0.38 g of the titled compound as a brown crystal (m.p.: 85° C.).

$^1$H-NMR (300 MHz, CDCl$_3$) δ: 1.70(t, J=6.9 Hz, 3H), 2.62(s, 3H), 3.27(m, 2H), 3.38(m, 2H), 3.96(s, 3H), 4.01(s, 3H), 4.14(s, 3H), 5.01(m, 2H), 5.78(s, 2H), 6.91(s, 1H), 7.25(s, 1H), 7.45(d, J=7.8 Hz, 1H), 7.92(d, J=9.6 Hz, 1H), 8.00(d, J=9.6 Hz, 1H), 8.24(d, J=9.3 Hz, 1H), 8.33(m, 1H), 10.30(s, 1H)

Example 7

Preparation of 5,6-dihydro-2,3-dimethoxybenzo[a]-13-ethyl-10-methoxy-9-(2-methoxy-5-nitro)benzyloxybenzo[g]quinolizinium chloride (Compound No. 7)

The process of Example 1 was repeated except that 0.67 g of 2-methoxy-5-nitrobenzyl bromide was employed in place of dodecyl bromide to give 0.55 g of the titled compound as a brown crystal (m.p.: 175° C.).

$^1$H-NMR (300 MHz, CDCl$_3$) δ: 1.69(t, J=6.3 Hz, 3H), 3.31(m, 2H), 3.42(m, 2H), 3.96(s, 3H), 4.00(s, 3H), 4.07(s, 3H), 4.08(s, 3H), 5.13(m, 2H), 5.74(s, 2H), 6.92(s, 1H), 7.92(d, J=9.3 Hz, 1H), 8.02(d, J=9.3 Hz, 1H), 8.25(d, J=2.7 Hz, 1H), 8.27(d, J=3.0 Hz, 1H), 8.54(d, J=3.0 Hz, 1H), 10.09(s, 1H)

Example 8

Preparation of 5,6-dihydro-2,3-dimethoxybenzo[a]-13-ethyl-10-methoxy-9-(4-vinyl)benzyloxybenzo[g]quinolizinium chloride (Compound No. 8)

The process of Example 1 was repeated except that 0.41 g of 4-vinylbenzyl chloride was employed in place of dodecyl bromide to give 0.33 g of the titled compound as a brown crystal (m.p.: 82° C.).

¹H-NMR (300 MHz, CDCl₃) δ: 1.69(t, J=6.8 Hz, 3H), 3.29(m, 2H), 3.40(m, 2H), 3.95(s, 3H), 4.00(s, 3H), 4.12(s, 3H), 5.01(m, 2H), 5.40(m, 2H), 5.68(s, 2H), 6.72(m, 1H), 6.92(s, 1H), 7.25(s, 2H), 7.38(m, 4H), 7.94(d, J=9.3 Hz, 1H), 7.99(d, J=9.3 Hz, 1H), 10.00(s, 1H).

Example 9

Preparation of 5,6-dihydro-2,3-dimethoxybenzo[a]-13-ethyl-10-methoxy-9-(4-trifluoromethyl)benzyloxybenzo[g]quinolizinium chloride (Compound No. 9)

The process of Example 1 was repeated except that 0.65 g of 4-(trifluoromethyl)benzyl bromide was employed in place of dodecyl bromide to give 0.72 g of the titled compound as a brown crystal (m.p.: 115° C.).

¹H-NMR (300 MHz, CDCl₃) δ: 1.66(t, J=7.5 Hz, 3H), 3.27(m, 2H), 3.38(m, 2H), 3.96(s, 3H), 4.00(s, 3H), 4.10(s, 3H), 5.08(m, 2H), 5.79(s, 2H), 6.91(s, 1H), 7.26(s, 1H), 7.66(d, J=9.3 Hz, 2H), 7.88(d, J=9.3 Hz, 2H), 7.97(d, J=7.8 Hz, 1H), 8.03(d, J=7.8 Hz, 1H), 10.24(s, 1H)

Example 10

Preparation of 5,6-dihydro-2,3-dimethoxybenzo[a]-9-(2-chloro-4-fluro)benzyloxy-13-ethyl-10-methoxybenzo[g]quinolizinium chloride (Compound No. 10)

The process of Example 1 was repeated except that 0.49 g of 2-chloro-4-fluorobenzyl bromide was employed in place of dodecyl bromide to give 0.19 g of the titled compound as a brown crystal (m.p.: 76° C.).

¹H-NMR (300 MHz, CDCl₃) δ: 1.61(t, J=6.3 Hz, 3H), 3.31(m, 2H), 3.40(m, 2H), 3.96(s, 3H), 4.01(s, 3H), 4.12(s, 3H), 4.91(m, 2H), 5.76(s, 2H), 6.99(s, 1H), 7.22(s, 1H), 7.34(m, 3H), 7.99(d, J=9.3 Hz, 1H), 8.08(d, J=9.3 Hz, 1H), 9.79(s, 1H)

Example 11

Preparation of 5,6-dihydro-2,3-dimethoxybenzo[a]-13-ethyl-10-methoxy-9-(3-trifluoromethyl)benzyloxybenzo[g]quinolizinium chloride (Compound No. 11)

The process of Example 1 was repeated except that 0.65 g of 3-(trifluoromethyl)benzyl bromide was employed in place of dodecyl bromide to give 0.42 g of the titled compound as a brown crystal (m.p.: 117° C.).

¹H-NMR (300 MHz, CDCl₃) δ: 1.66(t, J=6.8 Hz, 3H), 3.34(m, 2H), 3.38(m, 2H), 3.96(s, 3H), 4.00(s, 3H), 4.10(s, 3H), 5.00(m, 2H), 5.80(s, 2H), 6.91(s, 1H), 7.26(s, 1H), 7.60(m, 3H), 7.92(d, J=9.6 Hz, 1H), 8.00(d, J=9.6 Hz, 1H), 8.18(d, J=6.9 Hz, 1H), 10.23(s, 1H)

Example 12

Preparation of 5,6-dihydro-2,3-dimethoxybenzo[a]-13-ethyl-10-methoxy-9-(3-methoxy)benzyloxybenzo[g]quinolizinium chloride (Compound No. 12)

The process of Example 1 was repeated except that 0.42 g of 3-methoxybenzyl chloride was employed in place of dodecyl bromide to give 0.54 g of the titled compound as a brown crystal (m.p.: 70° C.).

¹H-NMR (300 MHz, CDCl₃) δ: 1.67(t, J=6.8 Hz, 3H), 3.21(m, 2H), 3.39(m, 2H), 3.87(s, 3H), 3.95(s, 3H), 4.00(s, 3H), 4.11(s, 3H), 5.00(m, 2H), 5.61(m, 2H), 6.99(s, 1H), 7.24(s, 1H), 7.27(m, 4H), 7.95(d, J=9.3 Hz, 1H), 8.00(d, J=9.3 Hz, 1H), 10.0(s, 1H).

Example 13

Preparation of 5,6-dihydro-2,3-dimethoxybenzo[a]-13-ethyl-10-methoxy-9-(2,3,5,6-tetrafluoro-4-trifluoromethyl)benzyloxy-benzo[g]quinolizinium chloride (Compound No. 13)

The process of Example 1 was repeated except that 0.84 g of 2,3,5,6-tetrafluoro-4-trifluoromethyl benzyl bromide was employed in place of dodecyl bromide to give 0.48 g of the titled compound as a brown crystal (m.p.: 85° C.).

¹H-NMR (300 MHz, CDCl₃) δ: 1.69(t, J=7.5 Hz, 3H), 3.30(m, 2H), 3.40(m, 2H), 3.96(s, 3H), 4.01(s, 3H), 4.07(s, 3H), 5.10(m, 2H), 5.96(s, 2H), 6.92(s, 1H), 7.25(s, 1H), 7.91(d, J=9.3 Hz, 1H), 8.05(d, J=9.3 Hz, 1H), 10.21(s, 1H)

Example 14

Preparation of 5,6-dihydro-2,3-dimethoxybenzo[a]-9-(4-benzyloxy)-benzyloxy-13-ethyl-10-methoxybenzo[g]quinolizinium chloride (Compound No. 14)

The process of Example 1 was repeated except that 0.63 g of 4-benzyloxybenzyl bromide was employed in place of dodecyl bromide to give 0.55 g of the titled compound as a brown crystal (m.p.: 71° C.).

¹H-NMR (300 MHz, CDCl₃) δ: 1.63(t, J=7.3 Hz, 3H), 3.41(m, 4H), 3.96(s, 3H), 3.99(s, 3H), 4.03(s, 3), 5.02(m, 2H), 5.59(s, 2H), 5.60(s, 2H), 6.87(s, 1H), 7.02(m, 2H), 7.35(m, 6H), 7.72(m, 2H), 7.93(d, J=9.3 Hz, 1H), 7.98(d, J=9.3 Hz, 1H), 9.89(s, 1H)

Example 15

Preparation of 5,6-dihydro-2,3-dimethoxybenzo[a]-9-(2,5-dimethyl)benzyloxy-13-ethyl-10-methoxybenzo[g]quinolizinium chloride (Compound No. 15)

The process of Example 1 was repeated except that 0.42 g of 2,5-dimethylbenzyl chloride was employed in place of dodecyl bromide to give 0.54 g of the titled compound as a brown crystal (m.p.: 72° C.).

¹H-NMR (300 MHz, CDCl₃) δ: 1.68(t, J=6.3 Hz, 3H), 2.40(m, 6H), 3.42(m, 4H), 3.95(s, 3H), 4.00(s, 3H), 4.10(s, 3H), 4.96(m, 2H), 5.70(s, 2H), 6.93(s, 1H), 7.13(m, 3H), 7.48(s, 1H), 7.95(d, J=9.3 Hz, 1H), 8.02(d, J=9.3 Hz, 1H), 9.88(s, 1H)

Example 16

Preparation of 5,6-dihydro-2,3-dimethoxybenzo[a]-13-ethyl-10-methoxy-9-(4-phenyl)benzyloxybenzo[g]quinolizinium chloride (Compound No. 16)

The process of Example 1 was repeated except that 0.55 g of 4-phenylbenzyl chloride was employed in place of dodecyl bromide to give 0.51 g of the titled compound as a brown crystal (m.p.: 83° C.).

¹H-NMR (300 MHz, CDCl₃) δ: 1.65(t, J=7.5 Hz, 3H), 3.26(m, 2H), 3.36(m, 2H), 3.95(s, 3H), 3.99(s, 3), 4.13(s, 3H), 5.04(m, 2H), 5.71(s, 2H), 6.90(s, 1H), 7.24(s, 1H), 7.37(d, J=7.2 Hz, 2H), 7.41(d, J=7.5 Hz, 2H), 7.46(d, J=7.2 Hz, 2H), 7.58(d, J=7.5 Hz, 2H), 7.86(d, J=9.3 Hz, 1H), 7.99(d, J=9.3 Hz, 1H), 10.09(s, 1H)

Example 17

Preparation of 5,6-dihydro-2,3-dimethoxybenzo[a]-9-(6-chloropyridine-3-yl)methoxy-13-ethyl-10-methoxybenzo[g]quinoli-zinium chloride (Compound No. 17)

The process of Example 1 was repeated except that 0.45 g of 3-chloromethyl-6-chloropyridine was employed in place of dodecyl bromide to give 0.28 g of the titled compound as a brown crystal (m.p.: 114° C.).

$^1$H-NMR (300 MHz, CDCl$_3$) δ: 1.67(t, J=7.5 Hz, 3H), 3.26(m, 2H), 3.38(m, 2H), 3.96(s, 3H), 4.01(s, 3H), 4.12(s, 3H), 5.13(m, 2H), 5.78(s, 2H), 6.91(s, 1H), 7.26(s, 1H), 7.42(d, J=8.4 Hz, 1H), 7.91(d, J=9.6 Hz, 1H), 8.00(d, J=9.6 Hz, 1H), 8.52(m, 1H), 8.66(m, 1H), 10.35(s, 1H)

Example 18

Preparation of 5,6-dihydro-2,3-dimethoxybenzo[a]-9-(3-chloro)benzyloxy-13-ethyl-10-methoxybenzo[g]quinolizinum chloride (Compound No. 18)

The process of Example 1 was repeated except that 0.45 g of 3-chlorobenzyl chloride was employed in place of dodecyl bromide to give 0.53 g of the titled compound as a brown crystal (m.p.: 165° C.).

$^1$H-NMR (300 MHz, CDCl$_3$) 5-1.66(t, J=7.5 Hz, 3H), 3.30(m, 2H), 3.38(m, 2H), 3.96(s, 3H), 4.00(s, 3H), 4.11(s, 3H), 5.06(m, 2H), 5.70(s, 2H), 6.91(s, 1H), 7.25(s, 1H), 7.38(m, 4H), 7.92(d, J=9.3 Hz, 1H), 8.00(d, J=9.3 Hz, 1H), 10.17(s, 1H)

Example 19

Preparation of 5,6-dihydro-2,3-dimethoxybenzo[a]-9-(4-bromo)benzyloxy-13-ethyl-10-methoxybenzo[g] quinolizinium chloride (Compound No. 19)

The process of Example 1 was repeated except that 0.69 g of 4-bromobenzyl bromide was employed in place of dodecyl bromide to give 0.17 g of the titled compound as a brown crystal (m.p.: 186° C.).

$^1$H-NMR (300 MHz, CDCl$_3$) δ: 1.66(t, J=7.8 Hz, 3H), 3.22(m, 2H), 3.37(m, 2H), 3.95(s, 3H), 4.00(s, 3H), 4.09(s, 3H), 5.04(m, 2H), 5.66(s, 2H), 6.91(s, 1H), 7.26(s, 1H), 7.35(d, J=8.4 Hz, 2H), 7.71(d, J=8.4 Hz, 2H), 7.88(d, J=9.6 Hz, 1H), 8.01(d, J=9.6 Hz, 1H), 10.13(s, 1H)

Example 20

Preparation of 5,6-dihydro-2,3-dimethoxybenzo[a]-13-ethyl-10-methoxy-9-(2-trifluoromethyl)benzyloxybenzo[g]quinolizinium chloride (Compound No. 20)

The process of Example 1 was repeated except that 0.65 g of 2-trifluoromethyl benzyl bromide was employed in place of dodecyl bromide to give 0.66 g of the titled compound as a brown crystal (m.p.: 72° C.).

$^1$H-NMR (300 MHz, CDCl$_3$) δ: 1.66(t, J=7.2 Hz, 3H), 3.31(m, 2H), 3.39(m, 2H), 3.96(s, 3H), 4.00(s, 3H), 4.04(s, 3H), 5.06(m, 2H), 5.82(s, 2H), 6.93(s, 1H), 7.26(s, 1H), 7.72(m, 3H), 7.94(d, J=9.6 Hz, 1H), 8.01(d, J=9.6 Hz, 1H), 8.39(d, J=7.2 Hz, 1H), 10.03(s, 1H)

Example 21

Preparation of 5,6-dihydro-2,3-dimethoxybenzo[a]-13-ethyl-10-methoxy-9-(3-phenoxy)benzyloxybenzo[g]quinolizinium chloride (Compound No. 21)

The process of Example 1 was repeated except that 0.60 g of 3-phenoxybenzyl chloride was employed in place of dodecyl bromide to give 0.40 g of the titled compound as a brown crystal (m.p.: 76° C.).

$^1$H-NMR (300 MHz, CDCl$_3$) δ: 1.66(t, J=7.5 Hz, 3H), 3.27(m, 2H), 3.37(m, 2H), 3.96(s, 3H), 4.00(s, 3H), 4.03(s, 3H), 5.09(m, 2H), 5.67(s, 2H), 6.92(s, 1H), 6.99(s, 1H), 7.01(m, 2H), 7.30(m, 6H), 7.62(m, 1H), 7.90(d, J=9.3 Hz, 1H), 7.98(d, J=9.3 Hz, 1H), 10.10(s, 1H)

Example 22

Preparation of 5,6-dihydro-2,3-dimethoxybenzo[a]-13-ethyl-10-methoxy-9-(4-methoxy)benzyloxybenzo[g]quinolizinium chloride (Compound No. 22)

The process of Example 1 was repeated except that 0.43 g of 4-methoxybenzyl chloride was employed in place of dodecyl bromide to give 0.84 g of the titled compound as a brown crystal (m.p.: 75° C.).

$^1$H-NMR (300 MHz, CDCl$_3$) δ: 1.68(t, J=7.2 Hz, 3H), 3.33(m, 2H), 3.42(m, 2H), 3.93(s, 3H), 3.94(s, 3H), 4.08(s, 3H), 5.23(m, 2H), 5.73(s, 2H1), 6.80(s, 1H), 6.95(s, 1H), 7.24(d, J=8.9 Hz, 2H), 7.39(d, J=8.7 Hz, 2H), 7.89(d, J=9.3 Hz, 1H), 7.97(d, J=9.3 Hz, 1H), 10.00(s, 1H)

Example 23

Preparation of 5,6-dihydro-2,3-dimethoxybenzo[a]-9-(2-chloro-6-fluoro)benzyloxy-13-ethyl-10-methoxybenzo[g]quinolizinium chloride (Compound No. 23)

The process of Example 1 was repeated except that 0.5 g of 2-chloro-6-fluorobenzyl chloride was employed in place of dodecyl bromide to give 0.54 g of the titled compound as a brown crystal (m.p.: 92° C.).

$^1$H-NMR (300 MHz, CDCl$_3$) δ: 1.66(t, J=7.2 Hz, 3H), 3.46(m, 4H), 3.96(s, 3H), 4.01(s, 3H), 4.12(s, 3H), 5.00(m, 2H), 5.75(s, 2H), 6.99(s, 1H), 7.11(s, 1H), 7.28(m, 3H), 7.99(d, J=9.3 Hz, 1H), 8.08(d, J=9.3 Hz, 1H), 9.74(s, 1H)

Example 24

Preparation of 5,6-dihydro-2,3-dimethoxybenzo[a]-13-ethyl-10-methoxy-9-(2-methyl-3-nitro)benzyloxybenzo[g]quinolizinium chloride (Compound No. 24)

The process of Example 1 was repeated except that 0.51 g of 2-methyl-3-nitrobenzyl chloride was employed in place of dodecyl bromide to give 0.45 g of the titled compound as a brown crystal (m.p.: 131° C.).

$^1$H-NMR (300 MHz, CDCl$_3$) δ: 1.68(t, J=7.5 Hz, 3H), 2.72(s, 3H), 3.35(m, 2H), 3.56(m, 2H), 3.96(s, 3H), 4.00(s, 3H), 4.09(s, 3H), 5.00(m, 2H), 5.85(s, 2H), 6.90(s, 1H), 7.44(d, J=8.4 Hz, 1H), 7.79(d, J=7.5 Hz, 1H), 7.92(d, J=9.3 Hz, 1H), 8.03(d, J=9.3 Hz, 1H), 8.42(d, J=6.9 Hz, 1H), 10.04(s, 1H)

Example 25

Preparation of 5,6-dihydro-2,3-dimethoxybenzo[a]-13-ethyl-10-methoxy-9-(5-methyl-2-nitro)benzyloxybenzo[g]quinolizinium chloride (Compound No. 25)

The process of Example 1 was repeated except that 0.51 g of 5-methyl-2-nitrobenzyl chloride was employed in place of dodecyl bromide to give 0.75 g of the titled compound as a brown crystal (m.p.: 98° C.).

¹H-NMR (300 MHz, CDCl₃) δ: 1.67(t, J=7.5 Hz, 3H), 2.60(s, 3H), 3.27(m, 2H), 3.42(m, 2H), 3.96(s, 3H), 4.00(s, 3H), 4.02(s, 3H), 5.19(m, 2H), 5.91(s, 2H), 6.92(s, 1H), 7.26(s, 1H), 7.93(d, J=9.3 Hz, I1H), 8.01(d, J=9.3 Hz, 1H), 8.03(m, 1H), 8.22(m, 1H), 10.23(s, 1H)

Example 26

Preparation of 5,6-dihydro-2,3-dimethoxybenzo[a]-13-ethyl-10-methoxy-9-allyloxybenzo[g]quinolizinium chloride (Compound No. 26)

The process of Example 1 was repeated except that 0.21 g of allyl chloride was employed in place of dodecyl bromide to give 0.30 g of the titled compound as a brown crystal (m.p.: 91° C.).

¹H-NMR (300 MHz, CDCl₃) δ: 1.67(t, J=7.5 Hz, 3H), 3.21(m, 2H), 3.43(m, 2H), 3.96(s, 3H), 4.00(s, 3H), 4.08(s, 3H), 5.11(m, 3H), 5.30(d, 1H, J=8.4 Hz), 5.50(d, J=15.7 Hz, 1H), 6.39(m, 1H), 6.95(s, 1H), 7.26(s, J=9.3 Hz, 1H), 7.94(d,J=9.3 Hz, 1H), 8.00(d, 1H), 10.14(s, 1H)

Example 27

Preparation of 5,6-dihydro-2,3-dimethoxybenzo[a]-9-(3,4-dimethyl)benzyloxy-13-ethyl-10-methoxybenzo[g]quinolizinium chloride (Compound No. 27)

The process of Example 1 was repeated except that 0.43 g of 3,4-dimethylbenzyl chloride was employed in place of dodecyl bromide to give 0.62 g of the titled compound as a brown crystal (m.p.: 167° C.).

¹H-NMR (300 MHz, CDCl₃) δ: 1.68(t, J=7.2 Hz, 3H), 2.20(m. 6H), 3.20(m, 2H), 3.42(m, 2H), 3.94(s, 3H), 4.08(s, 3H), 4.12(s, 3H), 5.16(m, 2H), 5.59(s, 2H), 6.93(s, 1H), 7.21(m, 4H), 7.94(m, 2H), 9.99(s, 1H)

Example 28

Preparation of 5,6-dihydro-2,3-dimethoxybenzo[a]-9-(2,4-dimethyl)benzyloxy-13-ethyl-10-methoxybenzo[g]quinolizimium chloride (Compound No. 28)

The process of Example 1 was repeated except that 0.43 g of 2,4-dimethylbenzyl chloride was employed in place of dodecyl bromide to give 0.59 g of the titled compound as a brown crystal (m.p.: 87° C.).

¹H-NMR (300 MHz, CDCl₃) δ: 1.68(t, J=7.2 Hz, 3H), 2.36(m, 6H), 3.25(m, 2H), 3.45(m, 2H), 3.93(s, 3H), 4.07(s, 3H), 4.10(s, 3H), 5.20(m, 2H), 5.72(s, 2H), 6.96(s, 1H), 7.07(m, 3H), 7.26(s, 1H), 7.88(q, J=9.3 Hz, 2H), 9.81(s, 1H)

Example 29

Preparation of 5,6-dihydro-2,3-dimethoxybenzo[a]-9-(1H-benzotriazol-1-yl)methoxy-13-ethyl-10-methoxybenzo[g]-quinolizinium chloride (Compound No. 29)

The process of Example 1 was repeated except that 0.46 g of 1-chloromethyl-1H-benzotriazole was employed in place of dodecyl bromide to give 0.65 g of the titled compound as a brown crystal (m.p.: 89° C.). 1H-NMR (300 MHz, CDCl₃) δ: 1.68(t, J=7.5 Hz, 3H), 3.18(m, 2H), 3.40(m, 2H), 3.95(s, 3H), 4.00(s, 3H), 4.01(s, 3H), 4.90(m, 2H), 5.80(s, 2H), 6.90(s, 1H), 7.09(s, 1H), 7.41(m, 2H), 7.67(m, 1H), 7.84(d, J=9.6 Hz, 1H), 8.01(d, J=9.6 Hz, 1H), 8.06(m, 1H), 8.35(d, J=8.7 Hz, 1H), 10.95(s, 1H)

Example 30

Preparation of 5,6-dihydro-2,3-dimethoxybenzo[a]-13-ethyl-9-[4-(i-propyl)benzyloxy]-10-methoxybenzo[g]quinolizinium chloride (Compound No. 30)

The process of Example 1 was repeated except that 0.46 g of 4-i-propylbenzyl chloride was employed in place of dodecyl bromide to give 0.40 g of the titled compound as a brown crystal (m.p.: 85° C.).

¹H-NMR (300 MHz, CDCl₃) δ: 1.23(s, 3H), 1.26(s, 3H), 1.65(t, J=7.5 Hz, 3H), 2.92(m, 1H), 3.29(m, 2H), 3.37(m, 2H), 3.95(s, 3H), 4.00(s, 3H), 4.12(s, 3H), 5.00(m, 2H), 5.62(s, 2H), 6.92(s, 1H), 7.25(s, 1H), 7.27(m, 2H), 7.69(d, J=8.1 Hz, 2), 7.93(d, J=9.3 Hz, 1H), 7.99(d, J=9.3 Hz, 1H), 9.98(s, 1H)

Example 31

Preparation of 5,6-dihydro-2,3-dimethoxybenzo[a]-13-ethyl-10-methoxy-9-(4-methyl)benzyloxybenzo[g]quinolizinium chloride (Compound No. 31)

The process of Example 1 was repeated except that 0.38 g of 4-methylbenzyl chloride was employed in place of dodecyl bromide to give 0.45 g of the titled compound as a brown crystal (m.p.: 87° C.).

¹H-NMR (300 MHz, CDCl₃) δ: 1.65(t, J=7.5 Hz, 3H), 2.35(s, 3H), 3.28(m, 2H), 3.37(m, 2H), 3.95(s, 3H), 4.00(s, 3H), 4.12(s, 3H), 5.00(m, 2H), 5.61(s, 2H), 6.92(s, 1H), 7.21(s, 1H), 7.25(d, J=5.7 Hz, 2H), 7.64(d, J=7.5 Hz, 2H), 7.93(d, J=9.3 Hz, 1H), 7.98(d, J=9.3 Hz, 1H), 9.95(s, 1H)

Example 32

Preparation of 5,6-dihydro-2,3-dimethoxybenzo[a]-13-ethyl-10-methoxy-9-(3-methyl)benzyloxybenzo[g]quinolizinium chloride (Compound No. 32)

The process of Example 1 was repeated except that 0.38 g of 3-methylbenzyl chloride was employed in place of dodecyl bromide to give 0.38 g of the titled compound as a brown crystal (m.p.: 76° C.).

¹H-NMR (300 MHz, CDCl₃) δ: 1.66(t, J=7.8 Hz, 3H), 2.41(s, 3H), 3.30(m, 2H), 3.52(m, 2H), 3.96(s, 3H), 4.00(s, 3H), 4.13(s, 3H), 5.01(m, 2H), 5.62(s, 2H), 6.92(s, 1H), 7.26(s, 1H), 7.29(m, 2H), 7.58(m, 2H), 7.93(d, J=9.3 Hz, 1H), 8.00(d, J=9.3 Hz, 1H), 9.97(s, 1H)

Example 33

Preparation of 5,6-dihydro-2,3-dimethoxybenzo[a]-13-ethyl-10-methoxy-9-(2-trifluoromethyl)benzyloxybenzo[g]quinolizinium chloride (Compound No. 33)

The process of Example 1 was repeated except that 0.38 g of 2-trifluoromethylbenzyl chloride was employed in place of dodecyl bromide to give 0.42 g of the titled compound as a brown crystal (m.p.: 85° C.).

¹H-NMR (300 MHz, CDCl₃) δ: 1.68(t, J=7.2 Hz, 3H), 2.58(s, 3H), 3.40(m, 4H), 3.95(s, 3H), 4.00(s, 3H), 4.09(s, 3H), 4.90(m, 2H), 5.69(s, 2H), 6.92(s, 1H), 7.24(s, 1H), 7.26(m, 2H), 7.79(m, 2H), 7.94(d, J=9.3 Hz, 1H), 8.01(d, J=9.3 Hz, 1H), 9.80(s, 1H)

Example 34

Preparation of 5,6-dihydro-2,3-dimethoxybenzo[a]-9-(3-bromo)benzyloxy-13-ethyl-10-methoxybenzo[g]quinolizinium chloride (Compound No. 34)

The process of Example 1 was repeated except that 0.68 g of 3-bromobenzyl chloride was employed in dodecyl bromide to give 0.52 g of the titled compound as a brown crystal (m.p.: 95° C.).

$^1$H-NMR (300 MHz, CDCl$_3$) δ: 1.60(t, J=7.5 Hz, 3H), 3.31(m, 2H), 3.52(m, 2H), 3.96(s, 3), 4.00(s, 3H), 4.11(s, 3H), 5.06(m, 2H), 5.69(s, 2H), 6.91(s, 1H), 7.26(s, 1H), 7.32(m, 2H), 7.49(m, 1H), 7.88(m, 1H), 7.92(d, J=9.3 Hz, 1H), 8.00(d,J=9.3 Hz, 1H), 10.15(s, 1H)

Example 35

Preparation of 5,6-dihydro-2,3-dimethoxybenzo[a]-9-(3,5-dimethoxy)benzyloxy-13-ethyl-10-methoxybenzo [g]quinolizinium chloride
(Compound No. 35)

The process of Example 1 was repeated except that 0.51 g of 3,5-dimethoxybenzyl chloride was employed in place of dodecyl bromide to give 0.26 g of the titled compound as a brown crystal (m.p.: 135° C.).

$^1$H-NMR (300 MHz, CDCl$_3$) δ: 1.68(t, J=7.8 Hz, 3H), 3.25(m, 2H), 3.36(m, 2H), 3.84(s, 6H), 3.95(s, 3H), 4.00(s, 3H), 4.11(s, 3H), 5.04(m, 2H), 5.56(s, 2H), 6.42(s, 1H), 6.92(s, 1H), 6.97(d, J=2.4 Hz, 2H), 7.24(s, 1H), 7.95(d, J=9.3 Hz, 1H), 8.00(d,J=9.3 Hz, 1H), 10.11(s, 1H)

Example 36

Preparation of 5,6-dihydro-2,3-dimethoxybenzo[a]-13-ethyl-10-methoxy-9-(quinolin-2-yl) methoxybenzo[g]quinolizinium chloride
(Compound No. 36)

The process of Example 1 was repeated except that 0.58 g of 2-chloromethyl quinoline was employed in place of dodecyl bromide to give 0.46 g of the titled compound as a brown crystal (m.p.: 104° C.).

$^1$H-NMR (300 MHz, CDCl$_3$) δ: 1.68(t, J=7.5 Hz, 3H), 3.27(m, 2H), 3.40(m, 2H), 3.97(s, 3H), 4.00(s, 3H), 4.09(s, 3H), 5.10(m, 2H), 5.96(s, 2H), 6.92(s, 1H), 7.25(s, 1H), 7.56(m, 2H), 7.73(m, 2H), 7.94(m, 2H), 8.19(d,J=8.4 Hz, 1H), 8.35(d, J=8.4 Hz, 1H), 10.23(s, 1H)

Example 37

Preparation of 5,6-dihydro-2,3-dimethoxybenzo[a]-13-ethyl-10-methoxy-9-(3,4,5-trimethoxy) benzyloxybenzo[g]quinolizinium chloride
(Compound No. 37)

The process of Example 1 was repeated except that 0.59 g of 3,4,5-trimethoxybenzyl chloride was employed in place of dodecyl bromide to give 0.60 g of the titled compound as a brown crystal (m.p.: 110° C.).

$^1$H-NMR (300 MHz, CDCl$_3$) δ: 1.68(t, J=7.5 Hz, 3H), 3.18(m, 2H), 3.41(m, 2H), 3.84(s, 3H), 3.87(s, 3H), 3.95(s, 3H), 3.95(s, 3H), 4.00(s, 3H), 4.14(s, 3H), 5.10(m, 2H), 5.61(s, 2H), 6.61(s, 1H), 6.90(s, 1H), 7.16(s, 1H), 7.25(s, 1H), 7.99(d, J=9.6 Hz, 1H), 8.00(d, J=9.6 Hz, 1H), 10.21(s, 1H)

Example 38

Preparation of 5,6-dihydro-2,3-dimethoxybenzo[a]-13-ethyl-10-methoxy-9-[4-(phenylsulfonylmethyl) benzyloxy]benzo[g]quinolizinium chloride
(Compound No. 38)

The process of Example 1 was repeated except that 0.89 g of 1-bromomethyl-2-[(phenylsulfonylmethyl)benzene was employed in place of dodecyl bromide to give 0.68 g of the titled compound as a brown crystal (m.p.: 100° C.).

$^1$H-NMR (300 MHz, CDCl$_3$) δ: 1.67(t, J=7.8 Hz, 3H), 3.28(m, 2H), 3.41(m, 2H), 3.96(s, 3H), 3.99(s, 3H), 4.26(s, 3H), 4.96(m, 4H), 5.67(s, 2H), 6.88(s, 1H), 7.03(s, 1H), 7.29(m, 2H), 7.44(m, 4H), 7.47(m, 2H), 7.61(m, 2H), 7.98 (d, J=9.3 Hz, 1H), 8.08(d, J=9.3 Hz, 1H), 8.17(d, J=6.6 Hz, 1H), 10.00(s, 1H)

Example 39

Preparation of 5,6-dihydro-2,3-dimethoxybenzo[a]-13-ethyl-10-methoxy-9-(5-nitrofuran-2-yl) methoxybenzo[g]quinolizinium chloride
(Compound No. 39)

The process of Example 1 was repeated except that 0.56 g of 2-bromomethyl-5-nitrofuran was employed in place of dodecyl bromide to give 0.18 g of the titled compound as a brown crystal (m.p.: 85° C.).

$^1$H-NMR (300 MHz, CDCl$_3$) δ: 1.69(t, J=7.2 Hz, 3H), 3.26(m, 2H), 3.38(m, 2H), 3.96(s, 3), 4.01(s, 3H), 4.18(s, 3H), 5.13(m, 2H), 5.80(s, 2H), 6.91(s, 1H), 7.26(s, 1H), 7.31(d, J=3.6 Hz, 1H), 7.46(d, J=3.6 Hz, 1H), 7.94(d, J=9.6 Hz, 1H), 8.03(d, J=9.6 Hz, 1H), 10.30(s, 1H)

Example 40

Preparation of 5,6-dihydro-2,3-dimethoxybenzo[a]-9-(6-chloro)piperonyloxy-13-ethyl-10-methoxybenzo[g]quinolizinium chloride
(Compound No. 40)

The process of Example 1 was repeated except that 0.56 g of 6-chloropiperonyl chloride was employed in place of dodecyl bromide to give 0.75 g of the titled compound as a brown crystal (m.p.: 105° C.).

$^1$H-NMR (300 MHz, CDCl$_3$) δ: 1.70(t, J=7.8 Hz, 3H), 3.38(m, 4H), 3.96(s, 3H), 3.99(s, 3H), 4.11(s, 3H), 4.82(m, 2H), 5.00(m, 2H), 5.59(s, 2H), 6.95(s, 1H), 7.26(s, 1H), 7.42(s, 1H), 7.51(s, 1H), 7.95(d, J=9.3 Hz, 1H), 8.09(d, J=9.3 Hz, 1H), 9.89(s, 1H)

Example 41

Preparation of 5,6-dihydro-2,3-dimethoxybenzo[a]-13-ethyl-10-methoxy-9-($^2$-methyl)propenoxybenzo [g]quinolizinium chloride (Compound No. 41)

The process of Example 1 was repeated except that 0.25 g of 3-chloro-2-methylpropene was employed in place of dodecyl bromide to give 0.46 g of the titled compound as a brown crystal (m.p.: 195° C.).

$^1$H-NMR (300 MHz, CDCl$_3$) δ: 1.68(t, J=7.8 Hz, 3H), 2.01(s, 3H), 3.39(m, 4H), 3.96(s, 3H), 4.00(s, 3H), 4.08(s, 3H), 5.05(m, 4H), 5.40(m, 2H), 6.93(s, 1H), 7.26(s, 1if), 7.91(d,J=9.3 Hz, 1H), 7.98(d, J=9.3 Hz, 1H), 10.01(s, 1H)

Example 42

Preparation of 5,6-dihydro-2,3-dimethoxybenzo[a]-13-ethyl-10-methoxy-9-(4-trifluoromethoxy) benzyloxybenzo[g]quinolizinium chloride
(Compound No. 42)

The process of Example 1 was repeated except that 0.69 g of 4-trifluoromethoxy benzyl bromide was employed in place of dodecyl bromide to give 0.49 g of the titled compound as a brown crystal (m.p.: 103° C.).

¹H-NMR (300 MHz, CDCl₃) δ: 1.63(t, J=7.5 Hz, 3H), 3.25(m, 2H), 3.46(m, 2H), 3.94(s, 3H), 4.00(s, 3H), 4.11(s, 3H), 5.24(m, 2H), 5.76(s, 2H), 6.84(s, 1H), 7.24(s, 1H), 7.25(d, J=9.6 Hz, 2H), 7.29(d, J=9.6 Hz, 2H), 7.93(d, J=9.3 Hz, 1H), 7.96(d, J=9.3 Hz, 1H), 10.54(s, 1H)

Example 43

Preparation of 5,6-dihydro-2,3-dimethoxybenzo[a]-13-ethyl-9-(2-iodo)benzyloxy-10-methoxybenzo[g] quinolizinium chloride (Compound No. 43)

The process of Example 1 was repeated except that 0.68 g of 2-iodobenzyl chloride was employed in place of dodecyl bromide to give 0.50 g of the titled compound as a brown crystal (m.p.: 110° C.).

¹H-NMR (300 MHz, CDCl₃) δ: 1.60(t, J=8.3 Hz, 3H), 3.35(m, 2H), 3.50(m, 2H), 3.96(s, 3H), 4.00(s, 3H1), 4.1l(s, 3H), 5.00(m, 2H), 5.65(s, 2H), 6.94(s, 1H), 7.07(m, 2H), 7.47(m, 2H), 7.96(d, J=9.3 Hz, 1H), 8.02(d, J=9.3 Hz, 1H), 10.00(s, 1H)

Example 44

Preparation of 5,6-dihydro-2,3-dimethoxybenzo[a]-13-ethyl-10-methoxy-9-[(3-trimethylsilyl)propen-2-yl]oxybenzo[g]quinolizinium chloride (Compound No. 44)

The process of Example 1 was repeated except that 0.44 g of 2-chloromethyl-3-trimethylsilyl-1-propene was employed in place of dodecyl bromide to give 0.59 g of the titled compound as a brown crystal (m.p.: 195° C.).

¹H-NMR (300 MHz, CDCl₃) δ: 1.63(t, J=7.8 Hz, 3H), 3.32(m, 2H), 3.41(m, 2H), 3.96(s, 3H), 4.00(s, 3H), 4.08(s, 3H), 5.05(m, 6H), 6.92(s, 1H), 7.26(s, 1H), 7.90(d, J=9.3 Hz, 1H), 7.98(d, J=9.3 Hz, 1H), 10.01(s, 1H)

Example 45

Preparation of 5,6-dihydro-2,3-methylenedioxybenzo[a]-9-dodecoxy-13-ethyl-10-methoxybenzo[g]quinolizinium iodide (Compound No. 45)

10 G of 5,6-dihydro-2,3-methylenedioxybenzo[a]-9,10-dimethoxy-13-ethylbenzo[g]quinolizinium chloride was subjected to pyrolysis under nitrogen atmosphere at a temperature of 180° C. and then dissolved in methanol. Undissolved by-products were filtered off and the residue was then purified by silica gel column chromatography eluting with a mixed solvent of methanol/dichloromethane (10:1) to give 6 g of 5,6-dihydro-2,3-methylenedioxybenzo[a]-13-ethyl-9-oxy-10-methoxy- benzo[g]quinolizinium salts as an orange crystal.

1 G of 5,6-dihydro-2,3-methylenedioxybenzo[a]-13-ethyl-9-oxy-10-methoxy-benzo[g]quinolizinium, 0.43 g of sodium iodide, and 0.39 g of potassium carbonate were dissolved in 10 ml of acetonitrile. After 0.71 g of dodecyl bromide was added thereto, the mixture was refluxed for 10 hours. Undissolved by-products were filtered off and the filtrate was concentrated under reduced pressure to remove the solvent. The residue was then dissolved in chloroform and washed with 10 ml of water. The organic solution was dried over magnesium sulfate to remove water and concentrated. The residue was then purified by silica gel column chromatography eluting with a mixed solvent of chloroform/methanol (15:1) to give 0.40 g of the titled compound as a brown crystal (m.p.: 175° C.).

¹H-NMR (300 MHz, CDCl₃) δ: 0.88(t, J=6.9 Hz, 3H), 1.28(m, 12H), 1.53(m, 4H), 1.69(t, J=7.2 Hz, 3H), 1.98(m, 4H), 3.35(m, 2H), 3.41(m, 2H), 4.41(s, 3H), 4.50(t, J=6.9 Hz, 2H), 5.10(m, 2H), 6.12(s, 2H), 6.93(s, 1H), 7.30(s, 1H), 8.00(d, J=9.3 Hz, 1H), 8.14(d, J=9.3 Hz, 1H), 10.01(s, 1H)

Example 46

Preparation of 5,6-dihydro-2,3-methylenedioxybenzo[a]-9-[(4-tert-butyl)benzyloxy]-13-ethyl-10-methoxybenzo [g] quinolizinium iodide (Compound No. 46)

The process of Example 45 was repeated except that 0.65 g of 4-(tert-butyl)benzyl bromide was employed in place of dodecyl bromide to give 0.82 g of the titled compound as a brown crystal (m.p.: 155° C.).

¹H-NMR (300 MHz, CDCl₃) δ: 1.29(s, 9H), 1.69(t, J=7.2 Hz, 3H), 3.22(m, 2H), 3.40(m, 2H), 4.11(s, 3H), 4.98(m, 2H), 5.53(s, 2H), 6.15(s, 2H), 6.97(s, 1H), 7.21(s, 1H), 7.44(d, J=8.1 Hz, 2H), 7.65(d, J=8.1 Hz, 2H), 8.05(d, J=9.3 Hz, 1H), 8.88(d, J=9.3 Hz, 1H), 10.02(s, 1H)

Example 47

Preparation of 5,6-dihydro-2,3-methylenedioxybenzo[a]-13-ethyl-10-methoxy-9-(2,3,4,5,6-pentafluoro)benzyloxybenzo[g]quinolizinium iodide (Compound No. 47)

The process of Example 45 was repeated except that 0.75 g of 2,3,4,5,6-pentafluorobenzyl bromide was employed in place of dodecyl bromide to give 0.92 g of the titled compound as a brown crystal (m.p.: 112° C.).

¹H-NMR (300 MHz, CDCl₃) δ: 1.69(t, J=7.8 Hz, 3H), 3.38(m, 2H), 3.40(m, 2H), 4.10(s, 3H), 5.06(m, 2H), 5.86(s, 2H), 6.12(s, 2H), 6.94(s, 1H), 7.29(s, 1H), 7.93(d, J=9.3 Hz, 1H), 8.04(d, J=9.3 Hz, 1H), 10.10(s, 1H)

Example 48

Preparation of 5,6-dihydro-2,3-methylenedioxybenzo[a]-9-(4,5-dimethoxy-2-nitro)benzyloxy-13-ethyl-10-methoxybenzo[g] quinolizinium iodide (Compound No. 48)

The process of Example 45 was repeated except that 0.79 g of 4,5-dimethoxy-2-nitrobenzyl bromide was employed in place of dodecyl bromide to give 0.49 g of the titled compound as a brown crystal (m.p.: 132° C.).

¹H-NMR (300 MHz, CDCl₃) δ: 1.61(t, J=7.2 Hz, 3H), 3.20(m, 2H), 3.39(m, 2H), 3.98(s, 3H), 4.01(s, 3H), 4.22(s, 3H), 5.18(m, 2H), 5.79(s, 2H), 6.13(s, 2H), 6.91(s, 1H, 7.23(s, 1H), 7.44(s, 1H), 7.70(s, 1H), 7.90(d, J=9.0 Hz, 1H), 8.00(d, J=9.0 Hz, 1H), 10.31(s, 1H)

Example 49

Preparation of 5,6-dihydro-2,3-methylenedioxybenzo[a]-13-ethyl-10-methoxy-9-(4-methyl-3-nitro)benzyloxybenzo[g]quinolizinium iodide (Compound No. 49)

The process of Example 45 was repeated except that 0.53 g of 4-methyl-3-nitrobenzyl chloride was employed in place of dodecyl bromide to give 0.50 g of the titled compound as a brown crystal (m.p.: 115° C.).

¹H-NMR (300 MHz, CDCl₃) (5 1.67(t, J=6.9 Hz, 3H), 2.61(s, 3H), 3.26(m, 2H), 3.35(m, 2H), 4.14(s, 3H), 5.01(m,

2H), 5.78(s, 2H), 6.13(s, 2H), 6.90(s, 1H), 7.23(s, 1H), 7.44(d, J=7.8 Hz, 1H), 7.92(d, J=9.6 Hz, 1H), 8.00(d,J=9.6 Hz, 1H), 8.24(d,J=9.3 Hz, 1H), 8.35(m, 1H), 10.18(s, 1H)

Example 50

Preparation of 5,6-dihydro-2,3-methylenedioxybenzo[a]-13-ethyl-10-methoxy-9-(4-trifluoromethyl)benzyloxy benzo[g]quinolizinium iodide (Compound No. 50)

The process of Example 45 was repeated except that 0.68 g of 4-trifluoromethyl benzyl bromide was employed in place of dodecyl bromide to give 0.75 g of the titled compound as a brown crystal (m.p.: 142° C.).

$^1$H-NMR (300 MHz, CDCl$_3$) δ: 1.67(t, J=7.5 Hz, 3H), 3.24(m, 2H), 3.37(m, 2H), 4.10(s, 3H), 5.08(m, 2H), 5.79(s, 2H), 6.15(s, 2H), 6.91(s, 1H), 7.26(s, 1H), 7.64(d, J=9.3 Hz, 2H), 7.86(d, J=9.3 Hz, 2H), 7.98(d, J=7.8 Hz, 1H), 8.03(d, J=7.8 Hz, 1H), 10.16(s, 1H)

Example 51

Preparation of 5,6-dihydro-2,3-methylenedioxybenzo[a]-13-ethyl-10-methoxy-9-(3-trifluoromethyl)benzyloxybenzo[g]quinolizinium iodide (Compound No. 51)

The process of Example 45 was repeated except that 0.68 g of 3-(trifluoromethyl)benzyl bromide was employed in place of dodecyl bromide to give 0.53 g of the titled compound as a brown crystal (m.p.: 134° C.).

$^1$H-NMR (300 MHz, CDCl$_3$) δ: 1.67(t, J=6.8 Hz, 3H), 3.34(m, 2H), 3.38(m, 2H), 4.10(s, 3H), 5.00(m, 2H), 5.80(s, 2H), 6.14(s, 2H), 6.91(s, 1H), 7.26(s, 1H), 7.62(m, 3H), 7.92(d, J=9.6 Hz, 1H), 8.00(d, J=9.6 Hz, 1H), 8.17(d, J=6.9 Hz, 1H), 10.14(s, 1H)

Example 52

Preparation of 5,6-dihydro-2,3-methylenedioxybenzo[a]-13-ethyl-10-methoxy-9-(2,3,5,6-tetrafluoro-4-trifluoromethyl)benzyloxybenzo[g]quinolizimium iodide (Compound No. 52)

The process of Example 45 was repeated except that 0.89 g of 2,3,5,6-tetrafluoro-4-trifluoromethyl benzyl bromide was employed in place of dodecyl bromide to give 0.99 g of the titled compound as a brown crystal (m.p.: 136° C.).

$^1$H-NMR (300 MHz, CDCl$_3$) δ: 1.67(t, J=7.5 Hz, 3H), 3.32(m, 2H), 3.40(m, 2H), 4.07(s, 3H), 5.10(m, 2H), 5.94(s, 2H), 6.11(s, 2H), 6.92(s, 1H), 7.25(s, 1H), 7.90(d,J=9.3 Hz, 1H), 8.04(d,J=9.3 Hz, 1H), 10.18(s, 1H)

Example 53

Preparation of 5,6-dihydro-2,3-methylenedioxybenzo[a]-13-ethyl-10-methoxy-9-(4-phenyl)benzloxybenzo[g]quinolizimium iodide (Compound No. 53)

The process of Example 45 was repeated except that 0.58 g of 4-phenylbenzyl chloride was employed in place of dodecyl bromide to give 0.69 g of the titled compound as a brown crystal (m.p.: 115° C.).

$^1$H-NMR (300 MHz, CDCl$_3$) J: 1.66(t, J=7.5 Hz, 3H), 3.24(m, 2H), 3.34(m, 2H), 4.13(s, 3H), 5.04(m, 2H), 5.71(s, 2H), 6.17(s, 2H), 6.90(s, 1H), 7.24(s, 1H), 7.38(d, J=7.2Hz, 2H), 7.42(d, J=7.5 Hz, 2H), 7.46(d, J=7.2 Hz, 2H), 7.58(d, J=7.5 Hz, 2H), 7.86(d, J=9.3 Hz, 1H), 8.00(d, J=9.3 Hz, 1H), 10.12(s, 1H)

Example 54

Preparation of 5,6-dihydro-2,3-methylenedioxybenzo[a]-9-(6-chloropyridinyl-3-yl)methoxy-13-ethyl-10-methoxybenzo[g]quinolizinium iodide (Compound No. 54)

The process of Example 45 was repeated except that 0.46 g of 3-chloromethyl-6-chloropyridine was employed in place of dodecyl bromide to give 0.44 g of the titled compound as a brown crystal (m.p.: 139° C.).

$^1$H-NMR (300 MHz, CDCl$_3$) δ: 1.68(t, J=7.5 Hz, 3H), 3.26(m, 2H), 3.38(m, 2H), 4.12(s, 3H), 5.14(m, 2H), 5.78(s, 2H), 6.11(s, 2H), 6.91(s, 1H), 7.26(s, 1H), 7.42(d, J=8.4 Hz, 1H), 7.90(d, J=9.6 Hz, 1H), 8.00(d, J=9.6 Hz, 1H), 8.52(m, 1H), 8.68(m, 1H), 10.25(s, 1H)

Example 55

Preparation of 5,6-dihydro-2,3-diethoxybenzo[a]-9-[4-(tert-butyl)benzyloxy]-13-ethyl-10-methoxybenzo[g]quinolizinium chloride (Compound No. 55)

To a solution of 10 g of 5,6-dihydro-2,3-dihydroxybenzo[a]-13-ethyl-9-hydroxy-10-methoxybenzo[g]quinolizinium chloride in 100ml of acetonitrile 8.1 g of potassium carbonate and 9.1 g of ethyl iodide. The mixture was refluxed for 5 hours. Undissolved by-products were filtered off and the filtrate was concentrated under reduced pressure to remove the solvent. The residue was then dissolved in chloroform and washed with 50 ml of water. The organic solution was dried over magnesium sulfate to remove water, filtered, and concentrated. The residue was then purified by silica gel column chromatography eluting with a mixed solvent of methanol/dichloromethane (2:1) to give 8.5 g of 5,6-dihydro-2,3-diethoxybenzo[a]13-ethyl-9-hydroxy-10-methoxybenzo[g]quinolizinium chloride as a light brown crystal.

To a solution of 1 g of 5,6-dihydro-2,3-diethoxybenzo[a]-13-ethyl-9-hydroxy-10-methoxy-benzo[g]quinolizinium chloride in 10 mg acetonitrile were added, 0.38 g of sodium iodide, and 0.35 g of potassium carbonate. After 0.58 g of 4-(tert-butyl)benzyl bromide was added thereto, the mixture was refluxed for 3 hours. Undissolved by-products were filtered off and the filtrate was concentrated under reduced pressure to remove the solvent. The residue was then dissolved in chloroform and washed with 10 ml of water. The organic solution was dried over magnesium sulfate to remove water, filtered, and concentrated. The residue was then purified by silica gel column chromatography eluting with a mixed solvent of chloroform/methanol (15:1) to give 0.72 g of the titled compound as a brown crystal (m.p.: 132° C.).

$^1$H-NMR (300 MHz, CDCl$_3$) δ: 1.29(s, 9H), 1.67(m, 9H), 3.24(m, 2H), 3.40(m, 2H), 4.04(m, 4H), 4.11(s, 3H), 4.99(m, 2H), 5.54(s, 2H), 6.94(s, 1H), 7.23(s, 1H), 7.40(d, J=9.3 Hz, 2H), 7.66(d, J=9.3 Hz, 2H), 8.04(d, J=9.3 Hz, 1H), 8.87(d, J=9.3 Hz, 1H), 10.11(s, 1H)

Example 56

Preparation of 5,6-dihydro-2,3-diethoxybenzo[a]-13-ethyl-10-methoxy-9-(2,3,4,5,6-pentafluoro)benzyloxybenzo[g]quinolizinium chloride (Compound No. 56)

The process of Example 55 was repeated except that 0.67 g of 2,3,4,5,6-pentafluorobenzyl bromide was employed in place of 4-(tert-butyl)benzyl bromide to give 0.82 g of the titled compound as a brown crystal (m.p.: 100° C.).

¹H-NMR (300 MHz, CDCl₃) δ: 1.67(m, 9H), 3.36(m, 2H), 3.42(m, 2H), 4.01(m, 4H), 4.08(s, 3H), 5.06(m, 2H), 5.86(s, 2H), 6.93(s, 1H), 7.28(s, 1H), 7.92(d, J=9.3 Hz, 1H), 8.04(d, J=9.3 Hz, 1H), 10.12(s, 1H)

Example 57

Preparation of 5,6-dihydro-2,3-diethoxybenzo[a]-9-(2,3,5,6-tetrafluoro-4-trifluoro methyl)benzyloxy-13-ethyl-10-methoxy-benzo [g]quinolizinium chloride (Compound No. 57)

The process of Example 55 was repeated except that 0.80 g of 2,3,5,6-tetrafluoro-4-trifluoromethyl benzyl bromide was employed in place of 4-(tert-butyl)benzyl bromide to give 0.68 g of the titled compound as a brown crystal (m.p.: 113° C.).

¹H-NMR (300 MHz, CDCl₃) δ: 1.69(m, 9H), 3.34(m, 21, 3.40(m, 2H), 3.96(m, 4H), 4.07(s, 3), 5.12(m, 2H), 5.96(s, 2), 6.92(s, 1H), 7.25(s, 1H), 7.92(d, 1H, J=9.6 Hz), 8.06(d, 1H, J=9.6 Hz), 10.24(s, 1H)

Example 58

Preparation of 5,6-dihydro-2,3-diethoxybenzo[a]-9-(6-chloropyridinyl-3-yl)methoxy-13-ethyl-10-methoxybenzo[g]quinolizinium chloride (Compound No. 58)

The process of Example 55 was repeated except that 0.42 g of 3-chloro-6-chloropyridine was employed in place of 4-(tert-butyl)benzyl bromide to give 0.42 g of the titled compound as a brown crystal (m.p.: 126° C.).

¹H-NMR (300 MHz, CDCl₃) δ: 1.68(m, 9H), 3.26(m, 2H), 3.38(m, 2H), 4.01(m, 4H), 4.12(s, 3H), 5.11(m, 2H), 5.78(s, 2H), 6.91(s, 1H), 7.26(s, 1H), 7.45(d, J=9.3 Hz, 1H), 7.91(d, J=9.6 Hz, 1H), 8.00(d, J=9.6 Hz, 1H), 8.52(m, 1H), 8.64(m, 1H), 10.30(s, 1H)

Example 59

Preparation of 5,6-dihydro-2,3-dihydroxybenzo[a]-13-ethyl-10-methoxy-9-(2,3,4,5,6-pentafluoro) benzyloxybenzo[g]quinolizinium chloride (Compound No. 59)

To a solution of 1 g of 5,6-dihydro-2,3-dihydroxybenzo [a]-13-ethyl-9-hydroxy-10-methoxy-benzo[g]quinolizinium chloride in 10 mg of acetonitrile were added 0.44 g of sodium iodide, and 0.41 g of potassium carbonate. After 0.77 g of 2,3,4,5,6-pentafluorobenzyl bromide was added thereto, the reaction mixture was stirred for 24 hours in an ice bath. After pH was adjusted to neutral with an aqueous hydrochloric acid solution, undissolved by-products were filtered off and the filtrate was concentrated under reduced pressure to remove the solvent. The residue was then dissolved in chloroform and washed with 10 ml of water. The organic solution was dried over magnesium sulfate to remove water filtered, and concentrated. The residue was then purified by silica gel column chromatography eluting with a mixed solvent of chloroform/methanol (15:1) to give 0.34 g of the titled compound as a brown crystal (m.p.: 82° C.).

¹H-NMR (300 MHz, DMSO-d₆) δ:1.47(t, 3H),3.12(m, 2H),3.34(m, 2H), 4.01(s, 3H), 4.82(m, 2H), 5.72(s, 2H), 7.17(s, 1H), 7.31(s, 1H), 8.19(d, J=7.2 Hz, 1H), 8.22(d, J=7.2 Hz, 1H), 9.95(s, 1H)

Example 60

Preparation of 5,6-dihydro-2,3-dihydroxybenzo[a]-13-ethyl-10-methoxy-9-(2,3,5,6-tetrafluoro-4-trifluoromethyl)benzyloxybenzo[g]quinolizinium chloride (Compound No. 60)

The process of Example 59 was repeated except that 0.92 g of 2,3,5,6-tetrafluoro-4-trifluoromethyl benzyl bromide was employed in place of 2,3,4,5,6-pentafluorobenzyl bromide to give 0.25 g of the titled compound as a brown crystal (m.p.: 88° C.).

¹H-NMR (300 MHz, DMSO-d₆) δ: 1.48(t,J=6.3 Hz, 3H), 3.18(m, 2H), 3.37(m, 2H), 4.07(s, 3H), 4.91(m, 2H), 5.77(s, 2H), 6.84(s, 1H), 7.11(s, 1H), 8.01(d, J=9.3 Hz, 1H), 8.07(d, J=9.3 Hz, 1H), 9.99(s, 1H)

Example 61

Preparation of 5,6-dihydro-2,3-diethoxybenzo[a]-9-dodecoxy-10-ethoxy-13-ethylbenzo[g]quinolizinium chloride (Compound No. 61)

To a solution of 10 g of 5,6-dihydro-2,3-methylenedioxybenzo[a]-9,10-dimethoxy-13-ethyl-benzo [g]quinolizinium chloride in 100 mg of dichloromethane was suspended 30 g of aluminum chloride and the mixture was stirred for 1 hour. The reaction mixture was concentrated under reduced pressure to remove the solvent. A 15% aqueous hydrochloric acid solution was added to the mixture and the precipitate produced was filtered, washed with water, and dried to give 7.5 g of 5,6-dihydro-2,3-dihydroxybenzo[a]-9,10-dihydroxy-13-ethylbenzo[g] quinolizinium chloride as dark brown crystal.

To a solution of 10 g of 5,6-dihydro-2,3-dihydroxybenzo [a]-9,10-dihydroxy-13-ethylbenzo-[g]quinolizinium chloride in 100 ml of acetonitrile were added 12.1 g of potassium carbonate and 14.3 g of ethyl iodide. The mixture was refluxed for 5 hours. Undissolved by-products were filtered off and the filtrate was concentraed under reduced pressure to remove the solvent. The residue was then dissolved in chloroform and washed with 50 ml of water. The organic solution was dried over magnesium sulfate to remove water, filterated, and concentrated. The residue was then purified by silica gel column chromatography eluting with a mixed solvent of methanol/dichloro-methane (2:1) to give 7.8 g of 5,6-dihydro-2,3-diethoxybenzo[a]-10-ethoxy-13-ethyl-9-hydroxybenzo[g]quinolizinium chloride as a light brown crystal.

To a solution of 1 g of 5,6-dihydro-2,3-diethoxybenzo[a]-10-ethoxy-13-ethyl-9-hydroxy-benzo[g]quinolizinium chloride in 10 mg of acetonitrile were added 0.37 g of sodium iodide and 0.34 g of potassium carbonate. After 0.62 g of dodecyl bromide was then added thereto, the mixture was refluxed for 10 hours. Undissolved by-products were filtered off and the filtrate was concentrated under reduced pressure to remove the solvent. The residue was then dissolved in chloroform and washed with 10 ml of water. The organic solution was dried over magnesium sulfate to remove water, filtered, and concentrated. The residue was then purified by silica gel column chromatography eluting with a mixed solvent of chloroform/methanol (15:1) to give 0.37 g of the titled compound as a brown crystal (m.p.: 174° C.).

¹H-NMR (300 MHz, CDCl₃) δ: 0.87(t, J=6.9 Hz, 3H), 1.24(m, 12H), 1.50(m, 4H), 1.68(m, 12H), 1.98(m, 4H), 3.34(m, 2H), 3.48(m, 2H), 4.01(m, 8H), 4.52(t, J=6.9 Hz, 2H), 5.20(m, 2H), 6.93(s, 1H), 7.30(s, 1H), 8.04(d, J=9.3 Hz, 1H), 8.13(d, J=9.3 Hz, 2H), 10.07(s, 1H)

Example 62

Preparation of 5,6-dihydro-2,3-diethoxybenzo[a]-10-ethoxy-13-ethyl-9-(4-trifluoromethyl)benzyloxy benzo[g]quinolizinium chloride (Compound No. 62)

The process of Example 61 was repeated except that 0.59 g of 4-trifluoromethyl benzyl bromide was employed in place of dodecyl bromide to give 0.83 g of the titled compound as a brown crystal (m.p.: 142° C.).

$^1$H-NMR (300 MHz, CDCl$_3$) δ: 1.69(m, 12H), 3.26(m, 2H), 3.34(m, 2H), 4.00(m, 12H), 5.08(m, 2H), 5.80(s, 2H), 6.93(s, 1H), 7.25(s, 1H), 7.68(d, J=9.6 Hz, 2H), 7.84(d, J=9.6 Hz, 2H), 7.96(d, J=7.4 Hz, 1H), 8.04(d, J=7.4 Hz, 1H), 10.21(s, 1H)

Example 63

Preparation of 5,6-dihydro-2,3-diethoxybenzo[a]-10-ethoxy-13-ethyl-9-(3-trifluoromethyl)benzyloxy enzo[g]quinolizinium chloride (Compound No. 63)

The process of Example 61 was repeated except that 0.59 g of 3-trifluoromethylbenzyl bromide was employed in place of dodecyl bromide to give 0.58 g of the titled compound as a brown crystal (m.p.: 127° C.).

$^1$H-NMR (300 MHz, CDCl$_3$) δ: 1.70(m, 12H), 3.32(m, 2H), 3.38(m, 2H), 4.10(m, 12H), 5.00(m, 2H), 5.85(s, 2H), 6.92(s, 1H), 7.26(s, 1H), 7.62(m, 3H), 7.92(d, J=9.6 Hz, 1H), 8.00(d, J=9.6 Hz, 1H), 8.18(d, J=6.9 Hz, 1H), 10.17(s, 1H)

Example 64

Preparation of 5,6-dihydro-2,3-diethoxybenzo[a]-10-ethoxy-13-ethyl-9-(2,3,5,6-tetrafluoro-4-trifluoromethyl)-benzyloxy benzo[g]quinolizinium chloride (Compound No. 64)

The process of Example 61 was repeated except that 0.77 g of 2,3,5,6-tetrafluoro-4-trifluoromethyl benzyl bromide was employed in place of dodecyl bromide to give 0.68 g of the titled compound as a brown crystal (m.p.: 110° C.).

$^1$H-NMR (300 MHz, CDCl$_3$) δ: 1.64(m, 12H), 3.30(m, 2H), 3.40(m, 2H), 4.07(m, 12H), 5.10(m, 2H), 5.98(s, 2H), 6.92(s, 1H), 7.25(s, 1H), 7.92(d, J=9.6 Hz, 1H), 8.06(d, J=9.6 Hz, 1H), 10.20(s, 1H)

Example 65

Preparation of 5,6-dihydro-2,3-diethoxybenzo[a]-9-(6-chloropyridine-3-yl)methoxy-10-ethoxy-13-ethylbenzo[g]-quinolizinium chloride (Compound No. 65)

The process of Example 61 was repeated except that 0.4 g of 3-chloromethyl-6-chloropyridine was employed in place of dodecyl bromide to give 0.37 g of the titled compound as a brown crystal (m.p.: 136° C.).

$^1$H-NMR (300 MHz, CDCl$_3$) δ: 1.68(m, 12H), 3.24(m, 2H), 3.38(m, 2H), 4.12(m, 12H), 5.13(m, 2H), 5.78(s, 2H), 6.90(s, 1H), 7.26(s, 1H), 7.41(d, J=9.3 Hz, 1H), 7.92(d, J=9.6 Hz, 1H), 8.00(d, J=9.6 Hz, 1H), 8.54(m, 1H), 8.66(m, 1H), 10.23(s, 1H)

Example 66

Preparation of 5,6-dihydro-2,3-dipropoxybenzo[a]-9-[4-(tert-butyl)benzyloxy]-13-ethyl-10-propoxybenzo[g]quinolizimium chloride (Compound No. 66)

To a solution of 10 g of 5,6-dihydro-2,3-dihydroxybenzo[a]-9,10-dihydroxy-13-ethylbenzo-[g]quinolizinium chloride in 100 ml of acetonitrile 12.1 g of potassium carbonate and 15.6 g of propyl iodide. The mixture was refluxed for 8 hours. Undissolved by-products were filtered off and the filtrate was concentraed under reduced pressure to remove the solvent. The residue was then dissolved in chloroform and washed with 50 ml of water. The organic solution was dried over magnesium sulfate to remove water, filtered and concentrated. The residue was then purified by silica gel column chromatography eluting with a mixed solvent of methanol/dichloromethane (2:1) to give 7.8 g of 5,6-dihydro-2,3-dipropoxybenzo[a]-13-ethyl-9-hydroxy-10-propoxybenzo[g]quinolizinium chloride as a light brown crystal.

To a solution of 1 g of 5,6-dihydro-2,3-dipropoxybenzo[a]-13-ethyl-9-hydroxy-10-propoxy-benzo[g]quinolizinium chloride in 10 mg of acetonitrile were added 0.34 g of sodium iodide and 0.31 g of potassium carbonate. After 0.51 g of 4-(tert-butyl)benzyl bromide was added thereto, the mixture was refluxed for 5 hours. Undissolved by-products were filtered off and the filtrate was concentrated under reduced pressure to remove the solvent. The residue was then dissolved in chloroform and washed with 10 ml of water. The solution was dried over magnesium sulfate to remove water, filtered, and concentrated. The residue was then purified by silica gel column chromatography eluting with a mixed solvent of chloroform/methanol (15:1) to give 0.68 g of the titled compound as a brown crystal (m.p.: 133° C.).

$^1$H-NMR (300 MHz, CDCl$_3$) δ: 1.29(s, 9H), 1.48(m, 9H), 1.72(m, 6H), 3.24(m, 2H), 3.45(m, 2H), 4.18(m, 6H), 4.99(m, 2H), 5.53(s, 2H), 6.95(s, 1H), 7.23(s, 1H), 7.44(d, J=9.6 Hz, 2H), 7.66(d, J=9.6 Hz, 2H), 8.07(d, J=9.3 Hz, 1H), 8.87(d, J=9.3 Hz, 1H), 10.05(s, 1H)

Example 67

Preparation of 5,6-dihydro-2,3-dipropoxybenzo[a]-13-ethyl-9-(2,3,4,5,6-pentafluoro)benzyloxy-10-propoxybenzo[g]quinolizinium chloride (Compound No. 67)

The process of Example 66 was repeated except that 0.59 g of 2,3,4,5,6-pentafluorobenzyl bromide was employed in place of 4-(tert-butyl)benzyl bromide to give 0.90 g of the titled compound as a brown crystal (m.p.: 122° C.).

$^1$H-NMR (300 MHz, CDCl$_3$) δ: 1.49(m, 9H), 1.59(m, 6H), 3.36(m, 2H), 3.40(m, 2H), 4.15(m 6H), 5.06(m, 2H), 5.84(s, 2H), 6.93(s, 1H), 7.28(s, 1H), 7.91(d, J=9.6 Hz, 1H), 8.05(d, J=9.6 Hz, 1H), 10.08(s, 1H)

Example 68

Preparation of 5,6-dihydro-2,3-dipropoxybenzo[a]-13-ethyl-10-propoxy-9-(4-trifluoromethyl)benzyloxybenzo[g]quinolizimium chloride (Compound No. 68)

The process of Example 66 was repeated except that 0.54 g of 4-trifluoromethylbenzyl bromide was employed in place of 4-(tert-butyl)benzyl bromide to give 0.95 g of the titled compound as a brown crystal (m.p.: 151° C.).

$^1$H-NMR (300 MHz, CDCl$_3$) δ: 1.50(m, 9H), 1.69(m, 6H), 3.24(m, 2H), 3.36(m, 2H), 4.10(m, 6H), 5.08(m, 2H), 5.79(s, 2H), 6.91(s, 1H), 7.26(s, 1H), 7.64(d, J=9.3 Hz, 2H), 7.86(d, J=9.3 Hz, 2H), 7.96(d, J=7.8 Hz, 1H), 8.02(d, J=7.8 Hz, 1H), 10.21(s, 1H)

Example 69

Preparation of 5,6-dihydro-2,3-dimethoxybenzo[a]-9-[4-(tert-butyl)-benzyloxy]-13-ethyl-10-methoxybenzo[g]quinolizinium bisulfate (Compound No. 69)

1 G of 8-acetonylated 5,6-dihydro-2,3-dimethoxybenzo[a]-9-[4-(tert-butyl)benzyloxy]-13-ethyl-10-methoxybenzo

[g]quinolizinium chloride was introduced into 10 ml of 1.0 M sulfuric acid. After the solution was stirred at room temperature for 2 hour, the precipitate produced was filtered, washed with 5 ml of water and then dried over oven to give 0.58 g of the titled compound as a brown crystal (m.p.: 123° C.).

$^1$H-NMR (300 MHz, CDCl$_3$) δ: 1.30(s, 9H), 1.70(t, J=7.2 Hz, 3H), 3.24(m, 2H), 3.40(m, 2H), 3.92(s, 3H), 3.99(s, 3H), 4.14(s, 3H), 4.98(m, 2H), 5.56(s, 2H), 6.97(s, 1H), 7.25(s, 1H), 7.46(d, J=8.11 Hz, 2H), 7.62(d, J=8.11 Hz, 2H), 8.02(d, J=9.3 Hz, 1H), 8.87(d, J=9.3 Hz, 114), 9.98(s, 1H)

Example 70

Preparation of 5,6-dihydro-2,3-dimethoxybenzo[a]-13-ethyl-10-methoxy-9-(2,3,4,5,6-pentafluoro) benzyloxybenzo[g]quinolizinium acetate
(Compound No. 70)

1 G of 8-acetonylated 5,6-dihydro-2,3-dimethoxybenzo [a]-13-ethyl-10-methoxy-9-(2,3,4,5,6-pentafluorobenzyloxybenzo[g]quinolizinium chloride was introduced into 10 ml of glacial acetic acid and the mixture was stirred at at room temperature for 5 hours. The precipitate produced was filtered, washed with 10 ml of ether and then dried over oven to give 0.75 g of the titled compound as a brown crystal (m.p.: 108° C.).

$^1$H-NMR (300 MHz, CDCl$_3$) δ: 1.62(t,J=7.8 Hz, 3H),3.35 (m, 2H),3.29(m, 2H), 3.96(s, 1H), 4.08(s, 3H), 4.14(s, 1H), 5.08(m, 2H), 5.86(s, 2H), 7.00(s, 1H), 7.23(s, 1H), 7.39(d, J=9.3 Hz, 1H), 8.04(d, J=9.3 Hz, 1H), 9.98(s, 1H)

Example 71

Preparation of 5,6-dihydro-2,3-dimethoxybenzo[a]-9-(6-chloropyridine-3-yl)methoxy-13-ethyl-10-methoxybenzo-[g]quinolizinium nitrate
(Compound No. 71)

1 G of 8-acetonylated 5,6-dihydro-2,3-dimethoxybenzo [a]-9-(6-chloropyridine-3-yl)methoxy-13-ethyl-10-methoxybenzo[g]quinolizinium chloride was introduced into 10 ml of 1.3 M nitric acid and the mixture was stirred at room temperature for 2 hour. The precipitate produced was filtered, washed with 5 ml of water and then dried over oven to give 0.82 g of the titled compound as a brown crystal (m.p.: 127° C.).

$^1$H-NMR (300 MHz, CDCl$_3$) δ: 1.62(t, J=7.5 Hz, 3H), 3.22(m, 2H), 3.32(m, 2H), 3.93(s, 3H), 4.00(s, 3H), 4.14(s, 3H), 5.10(m, 2H), 5.78(s, 2H), 6.90(s, 1H), 7.26(s, 1H), 7.44(d, J=8.4 Hz, 1H), 7.92(d, J=9.3 Hz, 1H), 8.00(d, J=9.3 Hz, 1H), 8.54(m, 1H), 8.68(m, 1H), 10.15(s, 1H)

Example 72

Inhibiting effect of 5,6-dihydrodibenzo[a,g] quinolizinium salts on sterol 14-reductase in microsome state.

Male Sprague-Dawley rats weighing from 150 to 250 g have been fed for 7 days with a diet containing 0.1% (w/w) Lovastatin and 5% (w/w) Cholestyramine. The animals were fasted for 12 hours before excising liver tissues and then sacrificed by decapitation at midnight. An aqueous solution containing 0.25 M of sucrose was injected into the hepatic portal vein to remove all the blood within the liver, and then, the liver was excised. The liver was homogenated with two volumes of buffer solution A (0.1 M potassium phosphate, 1 mM reduced glutathione, 0.5 mM EDTA, 20% (v/v) glycerol, pH 7.4) by repeating pestles over 10 times and then, centrifuged with 900×g for 5 minutes to give a supernatant. The supernatant was centrifuged with 12,000×g for 20 minutes. The supernatant obtained was ultracentrifuged with 105,000×g for 90 minutes to give a microsome which was used as an enzyme source of sterol 14-reductase. Assay for sterol 14-reductase was carried out as follows:

60 mmol of 4,4-dimethyl-5α-cholesta-7,14-dien-3p-ol and 5,6-dihydrodibenzo-[a,g]quinolizinium salts (compound no. 2) dissolved in DMSO were added to an assay mixture (total volume 1.0 ml) containing 2 mg of the microsomal protein, 2 mM of NADPH and 25 mg of glucose plus 20 units of glucose oxidase with preincubations under nitrogen at 37° C. for 4 min. unless otherwise specified to establish anaerobic condition. Buffer A (0.1 M potassium phosphate buffer, pH 7.4, including 1 mM reduced glutathione, 0.5 mM EDTA, and 20% (v/v) glycerol) used for incubation had been equilibrated with nitrogen, and nitrogen was exchanged for air in all sealed reaction flasks prior to the start of incubations. Incubation of the complete mixture was carried out anaerobically in sealed flasks for 10 min at 37° C. unless otherwise indicated. Incubations were terminated by the addition of 1 ml of ethanolic KOH followed by heating under reflux for 10 min. Sterols were extracted four times with 4 ml of petroleum ether, and the solvent was evaporated to dryness under a nitrogen stream. The resulting residue was dissolved in 200–500 μl of n-hexane for quantification by GLC at high sensitive attenuation. The activity of sterol 14-reductase was determined with the amount of the substrate wherein the double bonds of 14-carbon were reduced (for the amount reduced by 1 mg of the microsome protein for 1 minute). When the level of compound no. 2 added to the reaction system was 0.1 to 0.3 μM, 50% of inhibition of the enzymatic activity was observed.

Example 73

Effect of 5,6-dihydrodibenzo[a,g]quinolizimium salts on cholesterol biosynthesis ratio in CHO cells Chinese hamster ovary cells (CHO cell) were passage-cultivated on the flat plates. When colonies reached at 70 to 80% of area based on the total culture area, culture medium was replaced with a fresh medium and this was then used as samples for determining sterol 14-reductase activity and the cholesterol biosynthesis ratio.

Cholesterol biosynthesis ratio was determined by the Boogaard method [See, Biochem. J. 1987, 241, 345–51 ] with some modification. To the three dishes (diameter: 60 nm) containing the above CHO cells, the compound obtained from Example 2 were added and the mixture was then incubated for 30 minutes. After adding each 0.5 μCi of $^{14}$C-Mevalonate into the medium, incubation was continued for 2 hours. Culture medium was removed from the vessel, and the mixture was then washed 3 times with PBS at 4° C. The cells were scratched and collected in about 1.0 ml of PBS, and then subjected to centrifugation at 10,000 rpm for 5 min. In order to determine cholesterol having radioactivity, the cell precipitates were first floated with 0.1 N NaOH. After quantifying proteins in the floats, the floated material were taken so as to contain a suitable amount of proteins. The total volume was adjusted to 1.0 ml with the buffer solution A and added 1.0 ml of 25% ethanolic KOH solution thereto to proceed saponification reaction at 80° C. for 30 minutes. After dissolving unsaponicated sterols into n-hexane, they were separated by a thin layer liquid chromatography. The composition of the developing solvents was ethyl acetate and benzene at 95:5 ratio and cholesterol was developed as the internal standard for 50 minutes. Bands in the cholesterol-developed peak region were collected and put into a radioactive vial, and then 10 ml of scintillation cocktail solution were added thereto. The radioactivity strength of each sample was determined by a liquid scintillation counter (LSC) to give the cholesterol biosynthetic ratio. 50% of inhibitory effect was observed at the 0.1 to 0.3 µM concentration of 5,6-dihydrodibenzo[a,g] quinolizinium salts (compound no. 2).

Example 74

Effect of 5,6-dihydrodibenzo[a,g]quinolizinium salts on cholesterol biosynthesis in cultured human liver cell line (HepG2 cells)

Cultured human liver HepG2 cell line was grown on RPMI (Rosewell park Memorial Institute) 1640 culture medium containing 10% PBS until 60% of monolayer are formed in a 60 mm culture dish. After replacing the medium with 3 ml of a fresh culture medium containing 10% (v/v) LPDS (Fetal calf lipoprotein-deficient serum), the cells were further grown for 48 hours until 90% of cultivation degree appear. The culture medium was removed and the cell was then washed with PBS. 2 ml of culture medium containing compound no. 2 (final concentration 100 µM) and AY-9944 (final concentration 1 µM) were added thereto. Then, the medium was cultivated at 37° C. for 1 hour under the condition of 95% air/5% carbonic acid gas. AY-9944 which is an inhibitor for sterol 7-reductase was used as a control drug for assuring the present experimental procedure on the inhibition of cholesterol biosynthesis. Thereafter, 3 µCi of [1,2-$^{14}$C]acetate (72 mCi/mmol) were added thereto. The cultivation was continued for 2 hours so that the isotope is introduced into the cell and used as a precursor for sterol to be synthesized. Then, the culture medium was completely removed and washed with PBS twice and the cells were collected by scratching. 10 µg of cholesterol, 10 µg of lanosterol and [$^{3}$H]cholesterol (30,000 dpm) were added thereto, and saponification reaction was carried out at 70° C. for an hour by adding 7.5% of methanolic KOH solution. Unsaponified sterol was removed by extracting them three times with 3 ml of petroleum ether and dried with nitrogen purging. The dried samples were redissolved in 200 µl of chloroform. An aliquot of the samples was loaded onto Silicagel 60F thin layer plate and then separated using ethyl acetate/hexane 25/75 (v/v) as the developing solvent. The thin layer film was developed by exposure to Amersham Hyperfilm at −70° C. for 7 days. Cholesterol band were confirmed by comparing the band appeared in the film and that appeared in the iodine-stained thin layer. After scratching the cholesterol band, it was quantified by a liquid scintillation counter.

Example 75

In vivo effect of 5,6-dihydrodibenzo[a,g] quinolizinium salts on cholesterol biosynthesis in Syrian Golden Hamster Male Syrian Golden Hamsters weighing 90–110 g distributed from Samyuk Animal Laboratory, Seoul, Korea were bred under the following conditions: they were maintained under reverse light cycle (light cycle: from 6 P.M to 6 A.M; dark cycle: from 6 A.M. to 6 P.M.). The food and water were supplied at 10 A.M. The commercially available standard rodent chows were used. The hamsters were divided into 6 or 7 animals per group. The animals were fasted for 12 hours before administrating the drug. Then, 5,6-dihydrodibenzo[a,g]quinolizinium salts (compound no. 2) dissolved in a 0.25% methyl cellulose solution was administered orally for 14 days at the indicated time per a day. After fasting animals for 24 hours from the last administration, blood was extracted using a cardiac puncture and plasma was then isolated. Plasma lipids, i.e., total cholesterol, LDL-cholesterol, HDL-cholesterol and triglyceride values were analyzed using Automatic Analyzer (Hitachi 7150).

Example 76

Preparation of pharmaceutically available tablets of 5,6-dihydrodibenzo[a,g]quinolizinium salts The raw drug materials corresponding to an amount of 10,000 tablets were weighted and passed into 20 mesh sieve and the mixture was then blended for 10 minutes. The mixture was transferred to a compressor and was tableted under suitable pressure so as to give average weight of 200 mg per tablet.

| Component | amount |
|---|---|
| 1) Composition of the raw drug materials per tablet (200 mg) | |
| Compound No. 2 | 10 mg |
| Calcium carboxymethyl cellulose | 5 mg |
| Lactose #100 (100 mesh) | 147.5 mg |
| Hydroxypropyl cellulose | 5 mg |
| Ludipress (BASF AG) | 30 mg |
| Magnesium stearate | 2.5 mg |
| 2) Composition of the raw drug materials per tablet (200 mg) | |
| Compound No. 2 | 10 mg |
| Calcium carboxymethyl cellulose | 5 mg |
| Lactose #100 (100 mesh) | 147.5 mg |
| Hydroxypropyl cellulose | 5 mg |
| Kollidon VA64 (BASF AG) | 30 mg |
| Magnesium stearate | 2.5 mg |
| 3) Composition of the raw drug materials per tablet (200 mg) | |
| Compound No. 3 | 5 mg |
| Calcium carboxymethyl cellulose | 5 mg |
| Lactose #100 (100 mesh) | 152.5 mg |
| Hydroxypropyl cellulose | 5 mg |
| Ludipress (BASF AG) | 30 mg |
| Magnesium stearate | 2.5 mg |
| 4) Composition of the raw drug materials per tablet (200 mg) | |
| Compound No. 3 | 5 mg |
| Calcium carboxymethyl cellulose | 5 mg |
| Lactose #100 (100 mesh) | 152.5 mg |
| Hydroxypropyl cellulose | 5 mg |
| Kollidon VA64 (BASF AG) | 30 mg |
| Magnesium stearate | 2.5 mg |
| 5) Composition of the raw drug materials per tablet (200 mg) | |
| Compound No. 68 | 2 mg |
| Calcium carboxymethyl cellulose | 5 mg |
| Lactose #100 (100 mesh) | 155.5 mg |
| Hydroxypropyl cellulose | 5 mg |
| Ludipress (BASF AG) | 30 mg |
| Magnesium stearate | 2.5 mg |
| 6) Composition of the raw drug materials per tablet (200 mg) | |
| Compound No. 68 | 2 mg |
| Calcium carboxymethyl cellulose | 5 mg |
| Lactose #100 (100 mesh) | 155.5 mg |
| Hydroxypropyl cellulose | 5 mg |
| Kollidon VA64 (BASF AG) | 30 mg |
| Magnesium stearate | 2.5 mg |

INDUSTRIAL APPLICABILITY

The compounds of formula (I) can effectively inhibit sterol 14-reductase which is involved in the distal pathway of cholesterol biosynthesis, and thus, are especially effective in treating hypercholesterolemia.

The compounds of formula (I) above have the activities to decrease total cholesterol, LDL-cholesterol, and triglyceride levels and at the same time, to decrease glucose level in an animal test. Therefore, they are effective in diabetic hypercholesterolaemia and hyperlipidaemia.

Table 3 represents the relative activity for sterol 14-reductase of the compound of formula (I) as set forth in Table 1. Among the compounds of Table 1, Compound Nos. 2, 3, 9 and 68 markedly inhibited the cholesterol biosynthesis in human HepG2 cell line compared with AY9944 which is a comparative drug. In the animal test with Syrian Golden Hamster, Compound Nos. 2, 3, 9 and 68 have markedly decreased total cholesterol, LDL-cholesterol, and triglyceride levels compared with lovastatin which is a commercially available comparative cholesterol-lowering agent.

TABLE 3

Relative In Vitro activity for the compound of formula (I)

| Comp. No. | Enzyme Activity |
|---|---|
| 1 | +++ |
| 2 | +++ |
| 3 | +++ |
| 4 | ++ |
| 5 | +++ |
| 6 | +++ |
| 7 | ++ |
| 8 | + |
| 9 | +++ |
| 10 | ++ |
| 11 | +++ |
| 12 | + |
| 13 | +++ |
| 14 | + |
| 15 | + |
| 16 | +++ |
| 17 | +++ |
| 18 | ++ |
| 19 | ++ |
| 20 | ++ |
| 21 | + |
| 22 | + |
| 23 | ++ |
| 24 | + |
| 25 | + |
| 26 | + |
| 27 | + |
| 28 | + |
| 29 | ++ |
| 30 | + |
| 31 | + |
| 32 | + |
| 33 | + |
| 34 | ++ |
| 35 | + |
| 36 | ++ |
| 37 | + |
| 38 | ++ |
| 39 | ++ |
| 40 | + |
| 41 | + |
| 42 | ++ |
| 43 | ++ |
| 44 | + |
| 45 | ++ |
| 46 | +++ |
| 47 | +++ |
| 48 | +++ |
| 49 | ++ |
| 50 | ++ |
| 51 | ++ |
| 52 | ++ |
| 53 | ++ |

TABLE 3-continued

Relative In Vitro activity for the compound of formula (I)

| Comp. No. | Enzyme Activity |
|---|---|
| 54 | ++ |
| 55 | +++ |
| 56 | +++ |
| 57 | +++ |
| 58 | ++ |
| 59 | ++ |
| 60 | +++ |
| 61 | +++ |
| 62 | ++ |
| 63 | ++ |
| 64 | ++ |
| 65 | ++ |
| 66 | ++ |
| 67 | ++ |
| 68 | +++ |
| 69 | ++ |
| 70 | ++ |
| 71 | ++ |

+: 100 $\mu$M or more of $IC_{50}$ value
++: 10–100 $\mu$M of $IC_{50}$ value
+++: 1 $\mu$M or below of $IC_{50}$ value

TABLE 4

In vivo activity result for Comp. Nos. 2, 3, 9, and 68

| Group No. | n | Total cholesterol (mg/dl) | HDL cholesterol (mg/dl) | LDL cholesterol (mg/dl) | Triglyceride (mg/dl) |
|---|---|---|---|---|---|
| normal diet control | 5 | 130.8 ± 14 | 59.8 ± 7 | 37.0 ± 4 | 79.4 ± 13 |
| normal diet + lovastatin 6.0 mg/kg/day | 5 | 107.8 ± 9 (−17.6%) | 67.0 ± 3 (+11.2%) | 29.1 ± 2 (−21.4%) | 55.5 ± 7 (−30.1%) |
| normal diet + comp. 2 0.3 mg/kg/day | 5 | 115.8 ± 8 (−11.5%) | 66.6 ± 7 (+11.4%) | 31.0 ± 3 (−16.0%) | 67.8 ± 8 (−14.6%) |
| normal diet + Comp. 3 0.3 mg/kg/day | 5 | 89.0 ± 7 (−23.5%) | 63.0 ± 3.0 (+5.4%) | 18.8 ± 2 (−49.2%) | 49.2 ± 6 (−38.0%) |
| normal diet + Comp. 9 0.3 mg/kg/day | 5 | 82.4 ± 7 (−37.0%) | 56.2 ± 3.0 (−6.0%) | 20.2 ± 2 (−45.4%) | 44.8 ± 5.5 (−43.6%) |
| normal diet + Comp. 68 0.3 mg/kg/day | 5 | 87.4 ± 6 (−33.1%) | 58.6 ± 3 (−2.0%) | 21.8 ± 3 (−41.1%) | 45.2 ± 7 (−43.1%) |

Meanwhile, the toxicity of the compounds of the present invention was investigated as follows: i.e., the compounds were suspended into propylene glycol and then orally administered into each of 5 male and female SD rats at the age of 5-weeks that were fasted for 12 hours. Under the usual breeding conditions, general symptoms, weight change and lethal case of the above rats were monitored for two weeks. At the dose over 2,000 mg/kg of the compound nos. 2, 3, 9 and 68, general symptoms and the body weight change of the animals were normal and the lethal case was not observed. The toxicity data for the representative compounds (Compound No. 2, 3, 9 and 68) is set forth in Table 5.

TABLE 5

| Comp. No. | animal | administration route | sex | LD$_{50}$ |
|---|---|---|---|---|
| Comp. 2 | rats | oral | male | >2,000 |
|  |  |  | female | >2,000 |
| Comp. 3 | rats | oral | male | >2,000 |
|  |  |  | female | >2,000 |
| Comp. 9 | rats | oral | male | >2,500 |
|  |  |  | female | >2,000 |
| Comp. 68 | rats | oral | male | >3,000 |
|  |  |  | female | >3,000 |

As evident from the above descriptions, the compound of formula (I) inhibits sterol 14-reductase which is an enzyme in the distal stage of the cholesterol biosynthesis, thereby being effective in treatment of hypercholesterolemia and hyperlipidaemia and safe in an aspect of toxicity.

What is claimed is:

1. A pharmaceutical composition for treating hyperlipidaemia which comprises a 5,6-dihydrodibenzo[a,g]quinolizinium derivative represented by the formula (I), one or more salts of the derivative or a mixture thereof as an active ingredient:

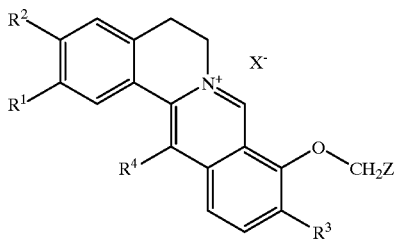

Formula (I)

wherein, $R^1$ and $R^2$ which may be the same or different from each other, represent a hydroxy group or an alkoxy group having 1 to 4 carbons or $R^1$ and $R^2$ together represent a methylenedioxy group;

$R^3$ represents a hydroxy group or an alkoxy group having 1 to 4 carbons;

$R^4$ represents an alkyl group having 2 to 8 carbons, or an alkenyl group having 3 to 8 carbons;

X represents an inorganic acid ion, an organic acid ion or a halide; and

Z represents an alkyl group having 5 to 12 carbons, or an alkenyl group having 4 to 6 carbons, a N-benzotriazolyl group, a quinolinyl group, a furyl group, a substituted furyl group, or a group represented by the formula:

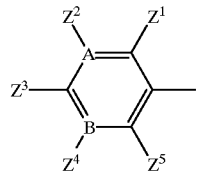

wherein $Z^1$, $Z^2$, $Z^3$, $Z^4$ and $Z^5$ which may be the same or different from each other, represent a hydrogen atom, halogen, an alkyl group having 1 to 5 carbons, a trifluoromethyl group, a phenyl group, a substituted phenyl group, a nitro group, an alkoxy group having 1 to 4 carbons, a methylenedioxy group, a trifluoromethoxy group, a hydroxy group, a benzyloxy group, a phenoxy group, a vinyl group, a benzenesulfonylmethyl group or a methoxycarbonyl group; and A and B, which may be the same or different from each other, represent carbon or nitrogen; and a pharmaceutically acceptable excipient.

2. The pharmaceutical composition according to claim 1, wherein Z represents a group having the following chemical formula

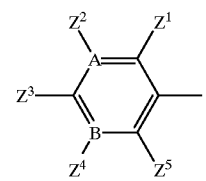

wherein $Z^1$, $Z^2$, $Z^3$, $Z^4$ and $Z^5$ which may be the same or different from each other, represent a hydrogen atom, halogen, an alkyl group having 1 to 5 carbons, a trifluoromethyl group, a phenyl group, a substituted phenyl group, nitro, an alkoxy group having 1 to 4 carbons, a methylenedioxy group, a trifluoromethoxy group, a hydroxy group, a benzyloxy group, a phenoxy group, a vinyl group, a benzenesulfonylmethyl group or a methoxycarbonyl group; and A and B which may be the same or different from each other, represent carbon or nitrogen; and X represents inorganic acid ion, organic acid ion or halide.

3. The pharmaceutical composition according to claim 1, wherein $R^4$ is ethyl group.

4. The pharmaceutical composition according to claim 1, wherein $R^1$ is a methoxy group, $R^2$ is a methoxy group, $R^3$ is a methoxy group, $R^4$ is an ethyl group, X is chloride, and Z represents 4-(tert-butyl)phenyl.

5. The pharmaceutical composition according to claim 1, wherein $R^1$ is a methoxy group, $R^2$ is a methoxy group, $R^3$ is a methoxy group, $R^4$ is an ethyl group, X is chloride, and Z represents 2,3,4,5,6-pentafluorophenyl.

6. The pharmaceutical composition according to claim 1, wherein $R^1$ is a methoxy group, $R^2$ is a methoxy group, $R^3$ is a methoxy group, $R^4$ is an ethyl group, X is chloride, and Z represents 4-trifluoromethylphenyl.

7. The pharmaceutical composition according to claim 1, wherein $R^1$ and $R^2$ each represent a methylenedioxy group, $R^3$ is a methoxy group, $R^4$ is an ethyl group, X is iodide, and Z represents 4-trifluoromethylphenyl.

8. The pharmaceutical composition according to claim 1, wherein said composition is sterol 14-reductase inhibitor.

9. The pharmaceutical composition according to claim 1, wherein X represents a nitrate, sulfate, acetate, tartrate, maleate, succinate, citrate, fumarate, aspartate, salicylate, glycerate, ascorbate, fluoride, chloride, iodide, or bromide.

* * * * *